United States Patent [19]

Meinke

[11] Patent Number: 5,177,063
[45] Date of Patent: Jan. 5, 1993

[54] AVERMECTIN COMPOUNDS WITH A 6,5-SPIROKETAL RING SYSTEM

[75] Inventor: Peter T. Meinke, New York, N.Y.

[73] Assignee: Merck & Co., Inc., Rahway, N.J.

[21] Appl. No.: 718,325

[22] Filed: Jun. 17, 1991

Related U.S. Application Data

[63] Continuation-in-part of Ser. No. 666,948, Mar. 11, 1991, abandoned.

[51] Int. Cl.$^5$ .................. A61K 31/70; A61K 31/365; C07D 315/00
[52] U.S. Cl. ..................................... 514/30; 514/450; 536/7.1; 549/264
[58] Field of Search ............... 549/264; 514/450, 30; 536/7.1

[56] References Cited

U.S. PATENT DOCUMENTS

| | | | |
|---|---|---|---|
| 3,950,360 | 4/1976 | Aoki et al. | 549/264 |
| 4,310,519 | 1/1982 | Albers-Schonberg et al. | 549/264 |
| 4,895,837 | 1/1990 | Mrozik et al. | 536/7.1 |
| 4,906,619 | 3/1990 | Eskola et al. | 514/450 |

FOREIGN PATENT DOCUMENTS

| | | |
|---|---|---|
| 319142 | 6/1989 | European Pat. Off. |
| 0340849 | 11/1989 | European Pat. Off. |
| 428286 | 5/1991 | European Pat. Off. |
| 1-056681 | 3/1989 | Japan |

OTHER PUBLICATIONS

T. L. Shih, et al. Tetra Letters vol. 31, No. 25 pp. 3525-3528.
T. L. Shih, et al. Tetra. Letters vol. 31, No. 25 pp. 3529-3532 (1990).

*Primary Examiner*—C. Warren Ivy
*Assistant Examiner*—Amelia A. Owens
*Attorney, Agent, or Firm*—David L. Rose; Joseph F. DiPrima

[57] ABSTRACT

Avermectin analogs are disclosed wherein the 6,6-spiroketal ring system has been reduced in size to a 6,5-spiroketal ring system by the deletion of the 25-position carbon atom and the 25-alkyl substituent. This is accomplished by opening the outer spiroketal ring with the elimination of ring carbon atoms 23, 24 and 25 and the alkyl substituent at the 25-position and incorporation a new component, reclosing the spiroketal to a 5-membered ring with new substituents at the 24-position. The compounds are used as anti-parasitic insecticidal and anti-helmintic agents in humans and animals and compositions containing such compounds as the active ingredient thereof are also disclosed.

14 Claims, No Drawings

AVERMECTIN COMPOUNDS WITH A 6,5-SPIROKETAL RING SYSTEM

CROSS-REFERENCE TO RELATED APPLICATIONS

This application is a continuation-in-part of application Ser. No. 666,948, filed Mar. 11, 1991, now abandoned.

BACKGROUND OF THE INVENTION

The avermectin compounds have been disclosed in a series of patents starting with U.S. Pat. No. 4,310,519 to Albers-Schoenberg, et al. The milbemycin compounds have been disclosed in a series of patents starting with U.S. Pat. No. 3,950,360 to Aoki, et al. All of the avermectins and milbemycins are characterized in having a 16-membered macrocyclic ring fused to a spiroketal ring system composed of two 6-membered rings. No references are known where this ring systems has been changed from the natural 6,6-system to the instant 6,5-system.

SUMMARY OF THE INVENTION

This invention is concerned with novel avermectin derivatives where the natural 6,6-spiroketal ring system has been contracted into a 6,5-spiroketal ring system. Thus it is an object of this invention to describe such novel compounds. It is a further object to describe the procedures for opening the outer 6-membered spiroketal ring and closing it into a 5-membered ring. A still further object is to describe the use of such compounds as anti-helmintic, anti-parasitic, acaricidal and nematocidal agents in human and animal health and in agriculture. A still further object is to describe compositions containing the instant compounds as the active ingredient thereof. Further objects will become apparent from a reading of the following description.

DESCRIPTION OF THE INVENTION

The compounds of the instant invention have the following structural formula:

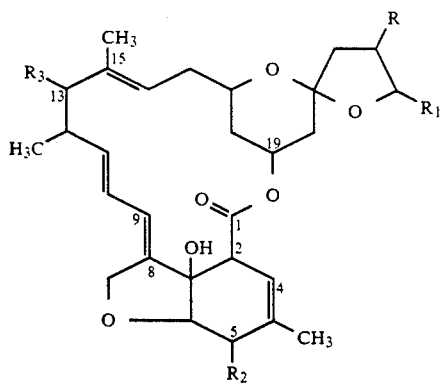

wherein R is hydrogen, $C_1$-$C_{10}$ alkyl, $C_2$-$C_{10}$ alkenyl or phenyl;

$R_1$ is hydrogen, $C_1$-$C_{10}$ alkyl, $C_2$-$C_{10}$ alkenyl, $C_2$-$C_{10}$ alkynyl, $C_1$-$C_{10}$ alkoxy $C_1$-$C_{10}$ alkyl or $C_1$-$C_{10}$ alkylthio $C_1$-$C_{10}$ alkyl group; a $C_3$-$C_8$ cycloalkyl or $C_5$-$C_8$ cycloalkenyl group, either of which may optionally be substituted by methylene or from 1 to 3 of $C_1$-$C_4$ alkyl groups or halo atoms; phenyl, phenoxy, $C_1$-$C_{10}$ alkyl phenyl, $C_2$-$C_{10}$ alkenyl phenyl, $C_2$-$C_{10}$ alkynyl phenyl, substituted $C_1$-$C_{10}$ alkyl wherein the substituents independently are 1 to 3 of $C_1$-$C_5$ alkyl, $C_3$-$C_8$ cycloalkyl or substituted $C_1$-$C_{10}$ alkyl wherein the substituents are independently 1 to 3 of hydroxy, halogen, cyano, $C_1$-$C_5$ alkyl thio, $C_1$-$C_5$ alkyl sulfinyl, $C_1$-$C_5$ alkyl sulfonyl, amino, $C_1$-$C_5$ mono or dialkyl amino, $C_1$-$C_5$ alkanoyl amino or $C_1$-$C_5$ alkanoylthio; or a 3 to 6 membered oxygen or sulfur containing heterocyclic ring which may be saturated, or fully or partly unsaturated and which may optionally be substituted independently by 1 to 3 of $C_1$-$C_5$ alkyl or halogen;

$R_2$ is hydroxy, $C_1$-$C_{10}$ alkoxy, $C_1$-$C_{10}$ alkanoyloxy, oxo or oxime;

$R_3$ is hydrogen, hydroxy, $C_1$-$C_{10}$ alkyloxy, $C_1$-$C_8$ alkanoyloxy, $C_1$-$C_5$ alkoxy-$C_1$-$C_5$-alkoxy, $C_1$-$C_5$ alkoxy-$C_1$-$C_5$-alkoxy-$C_1$-$C_5$-alkoxy, halogen,

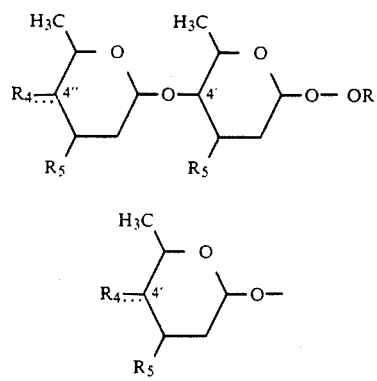

wherein $R_4$ is attached to C-4″ or C-4′ by a single bond and is hydroxy, amino, N—$C_1$-$C_8$ alkylamino, N,N—$C_1$-$C_8$-dialkylamino, N—$C_1$-$C_8$ alkanoylamino, N—$C_1$-$C_5$ alkyl $C_1$-$C_5$ alkanoylamino, tri $C_1$-$C_8$ alkylsilyloxy, $C_1$-$C_8$ alkylthio, $C_1$-$C_8$ alkyl sulfinyl, $C_1$-$C_8$ alkyl sulfonyl; or substituted $C_1$-$C_8$ alkylthio, sulfinyl of sulfonyl where the substituents are from 1 to 5 of hydroxy, halogen, amino or mono or di $C_1$-$C_3$ alkyl amino or $R_4$ is attached to C-4″ or C-4′ by a double bond and is ketone, oxime semicarbazono, N—$C_1$-$C_8$ alkylsemicarbazono, N,N—$C_1$-$C_8$ diloweralkylsemicarbazono, $C_1$-$C_8$ alkanoylhydrazono, benzoylhydrazono, or $C_1$-$C_8$ alkylbenzoyl-hydrazono; and each $R_5$ is independently hydroxy or $C_1$-$C_{10}$ alkoxy; or $R_4$ is

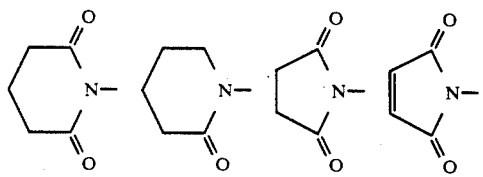

or $R_4$ is

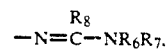

$$-N=C-NR_6R_7.$$
with $R_8$ above the C.

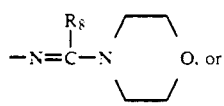

R$_4$ is —NH—CO—NR$_6$R$_7$.

R$_6$ and R$_7$ and R$_8$ are independently hydrogen or C$_1$-C$_{10}$ alkyl;

or R$_4$ is —NH—CN.

Preferred compounds of the instant invention are realized in the above structural formula when R is hydrogen, C$_1$-C$_{10}$ alkyl, C$_2$-C$_{10}$ alkenyl or phenyl;

R$_1$ is hydrogen, C$_1$-C$_{10}$ alkyl, C$_1$-C$_{10}$ alkoxy, C$_1$-C$_5$ alkoxy C$_1$-C$_5$ alkyl, C$_2$-C$_{10}$ alkenyl, C$_5$-C$_6$ cycloalkenyl, C$_3$-C$_8$ cycloalkyl, phenyl, substituted C$_1$-C$_{10}$ alkyl, or substituted phenyl wherein the substituents are halogen, C$_1$-C$_5$ alkyl, or C$_3$-C$_8$ cycloalkyl, substituted C$_1$-C$_{10}$ alkyl wherein the substituents are 1 to 3 of hydroxy, halogen, cyano, C$_1$-C$_5$ alkylthio, alkylsulfinyl, alkylsulfonyl, or C$_1$-C$_5$ alkanoylamino, or R$_1$ can be a 5- or 6-membered heterocyclic group selected from furanyl, tetrahydrofuranyl, thienyl, pyridyl, tetrahydropyran or piperidinyl;

R$_2$ is hydroxy, loweralkoxy or oxime;

R$_3$ is hydrogen, hydroxy, C$_1$-C$_{10}$ alkoxy, C$_1$-C$_8$ alkanoyloxy, C$_1$-C$_5$ alkoxy-C$_1$-C$_5$-alkoxy, C$_1$-C$_5$ alkoxy-C$_1$-C$_5$-alkoxy-C$_1$-C$_5$-alkoxy, halogen,

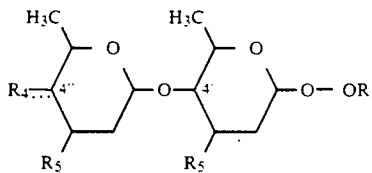

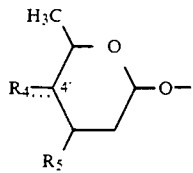

wherein R$_4$ is attached to C-4" or C-4' by a single bond and is hydroxy, amino, N—C$_1$-C$_8$ alkylamino, N,N—C$_1$-C$_8$-dialkylamino, N—C$_1$-C$_8$ alkanoylamino, N—C$_1$-C$_5$ alkyl, C$_1$-C$_5$ alkanoylamino, C$_1$-C$_3$ alkyl thio, C$_1$-C$_3$ alkylsulfinyl, C$_1$-C$_3$ alkylsulfonyl or substituted C$_1$-C$_3$ alkyl thio, sulfinyl or sulfonyl where the substituents are hydroxy, amino or trifluoro; or R$_4$ is attached to C-4" or C-4' by a double bond and is oxo; and each R$_5$ is independently hydroxy or C$_1$-C$_{10}$ alkoxy.

Still further preferred embodiments of the instant invention are realized in the above structural formula wherein:

R is hydrogen, C$_1$-C$_5$ alkyl, C$_2$-C$_5$ alkenyl or phenyl;

R$_1$ is hydrogen, C$_1$-C$_{10}$ alkyl, C$_1$-C$_{10}$ alkoxy, C$_1$-C$_5$ alkoxy C$_1$-C$_5$ alkyl, C$_2$-C$_{10}$ alkenyl, or C$_3$-C$_8$ cycloalkyl, phenyl, substituted C$_1$-C$_{10}$ alkyl, or substituted phenyl wherein the substituents are fluoro, substituted C$_1$-C$_{10}$ alkyl wherein the substituents are 1 to 3 of halogen, cyano, C$_1$-C$_5$ alkylthio, alkylsulfonyl, or C$_1$-C$_5$ alkanoylamino;

R$_2$ is hydroxy, methoxy or oxime;

R$_3$ is hydrogen, hydroxy, C$_1$-C$_5$ alkoxy-C$_1$-C$_5$-alkoxy, C$_1$-C$_5$ alkoxy-C$_1$-C$_5$-alkoxy-C$_1$-C$_5$-alkoxy, halogen, or

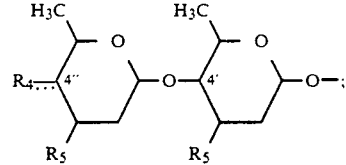

wherein R$_4$ is attached to C-4" or C-4' by a single bond and is hydroxy, amino, N—C$_1$-C$_3$ alkylamino, N,N—C$_1$-C$_3$-dialkylamino, N—C$_1$-C$_3$ alkanoylamino, or N—C$_1$-C$_3$ alkyl C$_1$-C$_5$ alkanoylamino; or R$_4$ is attached to C-4" or C-4' by a double bond and is oxo; and each R$_5$ is methoxy.

Additional preferred embodiments of the instant invention are realized in the structural formula wherein.

R is hydrogen, C$_1$-C$_5$ alkyl, C$_2$-C$_5$ alkenyl or phenyl;

R$_1$ is hydrogen, C$_1$-C$_6$ alkyl, C$_1$-C$_4$ alkoxy, C$_1$-C$_3$ alkoxy C$_1$-C$_3$ alkyl, C$_2$-C$_6$ alkenyl, or C$_5$-C$_6$ cycloalkyl, phenyl, substituted C$_1$-C$_6$ alkyl, or substituted phenyl wherein the substituents are fluoro, substituted C$_1$-C$_6$ alkyl wherein the substituent is hydroxy, fluoro, chloro, C$_1$-C$_3$ alkylthio, or C$_1$-C$_3$ alkanoylamino;

R$_2$ is hydroxy, methoxy or oxime;

R$_3$ is hydrogen, hydroxy, C$_1$-C$_3$ alkoxy-C$_1$-C$_3$-alkoxy, C$_1$-C$_3$ alkoxy-C$_1$-C$_3$-alkoxy-C$_1$-C$_3$-alkoxy, halogen, or

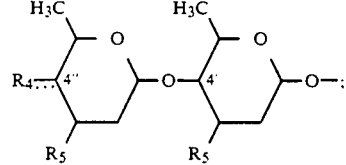

wherein R$_4$ is attached to C-4" or C-4' by a single bond and is hydroxy, amino, N—C$_1$-C$_3$ alkylamino, N,N—C$_1$-C$_3$-dialkylamino, N—C$_1$-C$_3$ alkanoylamino, or N—C$_1$-C$_3$ alkylalkanoylamino; and each R$_5$ is methoxy.

Additional preferred compounds of this invention are:

24-desmethyl-25-des-(2-butyl)-25-nor-24-cyanomethyl-22,23-dihydro avermectin B1a 24-desmethyl-25-des-(2-butyl)-25-nor-24-methylthiomethyl-22,23-dihydro avermectin B1a 24-desmethyl-25-des-(2-butyl)-25-nor-24-methylsulfoxymethyl-22,23-dihydro avermectin B1a 24-desmethyl-25-des-(2-butyl)-25-nor-24-methylsulfonylmethyl-22,23-dihydro avermectin B1a 24-desmethyl-25-des-(2-butyl)-25-nor-24-(2-imidazoylthio)methyl-22,23-dihydro avermectin B1a 24-desmethyl-25-des-(2-butyl)-25-nor-24-(4-pyridylthio)methyl-22,23-dihydro avermectin B1a 24-desmethyl-25-des-(2-butyl)-25-nor-24-[4-(2-oxo-but-3-ene)]-22,23-dihydro avermectin B1a 24-desmethyl-25-des-(2-butyl)-25-nor-24-acetoxymethyl-22,23-dihydro avermectin B1a 24-desmethyl-25-des-(2-butyl)-25-nor-24-[2-(4-methyl pent-2-enyl)]-22,23-dihydro avermectin B1a 24-desmethyl-25-des-(2-butyl)-25-nor-24-fluoromethyl-22,23-dihydro avermectin B1a 4''-deoxy-4''-epi-acetylamino-24-desmethyl-25-des-(2-butyl)-25-nor-24-isopropyl-22,23-dihydro avermectin B1a 4''-deoxy-4''-epi-acetylamino-24-desmethyl-25-des-(2-butyl)-25-nor-24-tert-butyl-22,23-dihydro avermectin B1a 4''-deoxy-4''-epi-acetylamino-24-desmethyl-25-des-(2-butyl)-25-nor-24-cyclohexyl-22,23-dihydro avermectin B1a 4''-deoxy-4''-epi-acetylamino-24-desmethyl-25-des-(2-butyl)-25-nor-24-phenyl-22,23-dihydro avermectin B1a 24-desmethyl-25-des-(2-butyl)-25-nor-24-phenyl-22,23-dihydro avermectin B1a aylcone 24-desmethyl-25-des-(2-butyl)-25-nor-24-isopropyl-22,23-dihydro avermectin B1a agylcone 24-desmethyl-25-des-(2-butyl)-25-nor-24-tert-butyl-22,23-dihydro avermectin B1a agylcone 24-desmethyl-25-des-(2-butyl)-25-nor-24-cyclohexyl-22,23-dihydro avermectin B1a agylcone 13-deoxy-13-fluoro-24-desmethyl-25-des-(2-butyl)-25-nor-24-phenyl-22,23-dihydro avermectin B1a agylcone 13-deoxy-13-fluoro-24-desmethyl-25-des-(2-butyl)-25-nor-24-isopropyl-22,23-dihydro avermectin B1a agylcone 24-desmethyl-25-des-(2-butyl)-25-nor-24-(1-cyclohexenyl)-22,23-dihydro avermectin B1a 13-deoxy-13-fluoro-24-desmethyl-25-des-(2-butyl)-25-nor-24-tert-butyl-22,23-dihydro avermectin B1a agylcone 13-O-methoxymethyl-24-desmethyl-25-des-(2-butyl)-25-nor-24-phenyl-22,23-dihydro avermectin B1a agylcone 13-O-methoxymethyl-24-desmethyl-25-des-(2-butyl)-25-nor-24-isopropyl-22,23-dihydro avermectin B1a agylcone 13-O-methoxymethyl-24-desmethyl-25-des-(2-butyl)-25-nor-24-cyclohexyl-22,23-dihydro avermectin B1a agylcone 13-O-methoxymethyl-24-desmethyl-25-des-(2-butyl)-25-nor-24-tert-butyl-22,23-dihydro avermectin B1a agylcone 13-O-methoxyethoxymethyl-24-desmethyl-25-des-(2-butyl)-25-nor-24-tert-butyl-22,23-dihydro avermectin B1a agylcone 13-O-methoxyethoxymethyl-24-desmethyl-25-des-(2-butyl)-25-nor-24-isopropyl-22,23-dihydro avermectin B1a agylcone 13-O-methoxyethoxymethyl-24-desmethyl-25-des-(2-butyl)-25-nor-24-cyclohexyl-22,23-dihydro avermectin B1a agylcone 13-O-methoxyethoxymethyl-24-desmethyl-25-des-(2-butyl)-25-nor-24-phenyl-22,23-dihydro avermectin B1a agylcone 13-deoxy-24-desmethyl-25-des-(2-butyl)-25-nor-24-phenyl-22,23-dihydro avermectin B1a agylcone 24-Desmethyl-25-des(2-butyl)-22,23-dihydro-25-nor-Avermectin B1a 24-Desmethyl-25-des(2-butyl)-22,23-dihydro-25-nor-24-methyl-Avermectin B1a 24-Desmethyl-25-des(2-butyl)-22,23-dihydro-25-nor-24-i-propyl-Avermectin B1a 24-Desmethyl-25-des(2-butyl)-22,23-dihydro-25-nor-24-t-butyl-Avermectin B1a 24-Desmethyl-25-des(2-butyl)-22,23-dihydro-25-nor-24-cyclohexyl-Avermectin B1a 24-Desmethyl-25-des(2-butyl)-22,23-dihydro-25-nor-24-methoxy-Avermectin B1a 24-Desmethyl-25-des(2-butyl)-22,23-dihydro-25-nor-24-phenyl-Avermectin B1a 24-Desmethyl-25-des(2-butyl)-22,23-dihydro-25-nor-24-(4-fluoro)phenyl-Avermectin B1a 24-Desmethyl-25-des(2-butyl)-22,23-dihydro-25-nor-24-(4-methoxy)phenyl-Avermectin B1a 24-Desmethyl-25-des(2-butyl)-22,23-dihydro-25-nor-24-(2-furyl)-Avermectin B1a 24-Desmethyl-25-des(2-butyl)-22,23-dihydro-25-nor-24-methoxymethyl-Avermectin B1a 24-Desmethyl-25-des(2-butyl)-22,23-dihydro-25-nor-24-phenoxymethyl-Avermectin B1a 24-Desmethyl-25-des(2-butyl)-22,23-dihydro-25-nor-24-n-octyl-Avermectin B1a 24-Desmethyl-25-des(2-butyl)-22,23-dihydro-5-ketoxime-25-nor-24-phenyl-Avermectin B1a 24-Desmethyl-25-des(2-butyl)-22,23-dihydro-5-ketoxime-25-nor-24-t-butyl-Avermectin B1a isomer A 24-Desmethyl-25-des(2-butyl)-22,23-dihydro-5-ketoxime-25-nor-24-t-butyl-Avermectin B1a isomer B 24-Desmethyl-25-des(2-butyl)-22,23-dihydro-5-ketoxime-25-nor-24-i-propyl-Avermectin B1a isomer A 24-Desmethyl-25-des(2-butyl)-22,23-dihydro-5-ketoxime-25-nor-24-t-butyl-Avermectin B1a isomer B 13-deoxy-24-desmethyl-25-des(2-butyl)-25-nor-22,23-dihydro-24-isopropyl-avermectin B1a aglycone 13-deoxy-24-desmethyl-25-des(2-butyl)-25-nor-22,23-dihydro-24-(t-butyl)-avermectin B1a aglycone 13-deoxy-24-desmethyl-25-des(2-butyl)-25-nor-22,23-dihydro-24-cyclohexyl-avermectin B1a aglycone 13-deoxy-24-desmethyl-25-des(2-butyl)-25-nor-22,23-dihydro-24-phenyl-avermectin B1a aglycone The instant compounds are prepared according to the following reaction scheme which, for clarity, depicts only that portion of the molecule containing carbon atoms 17–25 of the naturally occuring avermectins and milbemycins.

-continued
REACTION SCHEME

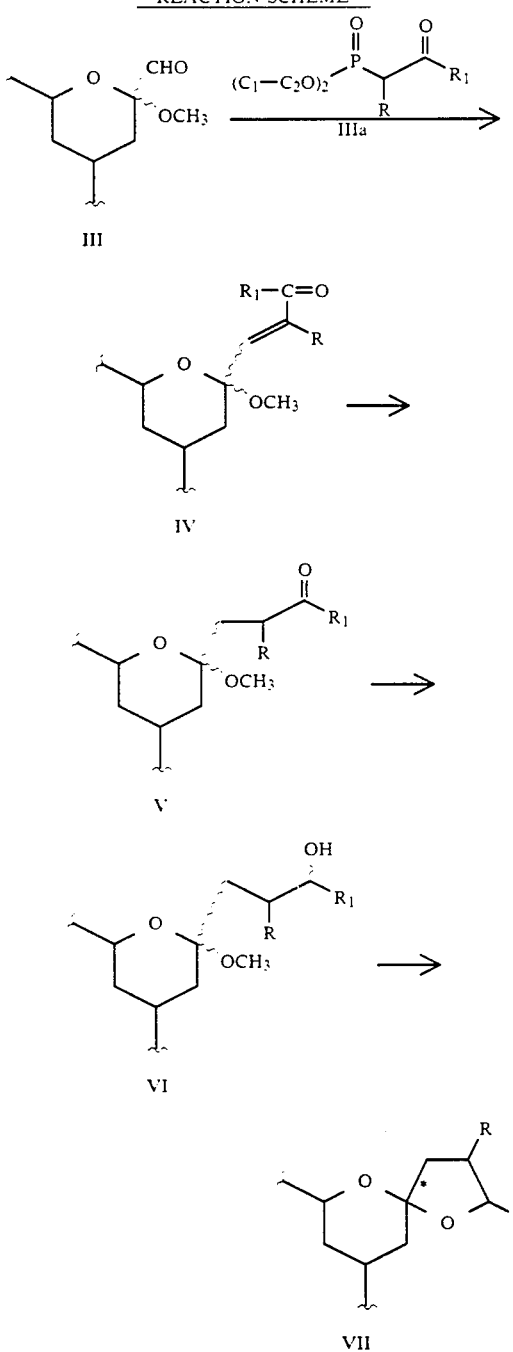

In the above Reaction Scheme the $R_{25}$ group is the 25-position group which is found in the natural avermectin and milbemycin compounds which are generally alkyl groups. It is noted that the foregoing process removes the natural 25-position group and replaces it in the analagous position of the new 6,5-spiroketal ring system by a new group $R_1$. The nature of the $R_1$ group is very broadly construed and it can be any group provided by the $R_1$ containing reagent Compound IIIa or by the addition of the appropriate nucleophiles to the $C_{24}$ aldehyde of Compound V. In addition, the use of the term "lower" to describe any at the reagents or solvents used in the preparation at the instant compounds defines such compounds or substituent groups on such compounds as having 1 to 6 carbon atoms.

The compounds of the instant invention can be prepared by reacting the critical intermediate III with the $R_1$ substituted phosphonate compound IIIa. The critical intermediate III is in six steps prepared from avermectin starting material I (avermectin B1a) with the 6,6-spiroketal ring system and the appropriate substituents $R_2$ and $R_3$ at positions 5 and 13 respectively, or with a substitution pattern from which the $R_2$ and $R_3$ groups can be prepared after the synthesis of the 6,5-spiro-ketal ring system of the instant compounds.

Compound I, suitably protected at the hydroxy groups, is reacted with an oxidizing agent such as oxalyl chloride in DMSO in the presence of at least 2 equivalents of a base to react with the HCl liberated during the course of the reaction. The reaction is carried out initially in the cold at temperatures less than 0° C. and preferably less than $-50°$ C. and is generally complete in from 1 to 10 hours affording the 23-keto compound.

In the next step the 23-keto compound is reacted with an alkali metal bis(trimethylsilyl)amide to form the enol ether with a 22,23-double bond. The reaction is carried out in the cold at a temperature less than 0° C. and preferably less than $-50°$ C. under an inert atmosphere in a non-reactive solvent such as a hydrocarbon, preferably an alkane or other nonpolar solvents such as tetrahydrofuran that will remain liquid at reaction temperatures. Generally mixtures of $C_7$ to $C_9$ alkanes, preferably hexanes, are used. The reaction is generally complete in from 1 to 10 hours. The choice of the base in this reaction is very important since it is well known that strong bases readily epimerize the 2-position and rearrange the 3,4-double bond to give analogs of low biological potency. It was found that from a selection of numerous bases, an alkali metal bis(trimethylsilyl)amide is capable of forming the desired silyl enol ether without any further side reactions.

In the next step the 22,23-double bond is epoxidized with a mild oxidizing agent, preferably a peroxy acid such as meta chloroperbenzoic acid. The reaction is carried out in an inert solvent such as a chlorinated hydrocarbon such as chloroform or methylene chloride and the like at a temperature of from 0° to 50° C. and is generally complete in about 10 minutes to 2 hours.

In the final step of the reaction of compound I to prepare compound II the 22,23-epoxide is treated with acidic methanol to hydrolize the epoxide and form compound II. The reaction is carried out at about room temperature and is generally complete in from 5 minutes to 2 hours.

In the foregoing series of reactions the intermediates may be isolated and purified, however it has not been found necessary to do so and if desired, the reactions may be carried out in a single reaction vessel, only isolating compound II at the conclusion of the series of four reaction steps.

Compound II is then cleaved to form the critical intermediate III in 2 steps. In the first step compound II is treated with lead tetraacetate which cleaves the 22,23-bond affording an intermediate where the 22-carbon is an aldehyde and the 23-carbon is a carboxylic acid or the methyl ester thereof. This compound is transketalized in a lower alkanol, preferably methanol to cleave carbons 22 to 25 and replace them with the alcohol residue, preferably a methyl group, affording compound III. The reaction is carried out at from 0° C. to room temperature and is generally complete in from 1 to 2 hours. The product is isolated using techniques known to those skilled in the art.

Compound III is reacted with the $R_1$ substituted phosphonate IIIa or similar reagents such as $R_1$ substituted ($\beta$-keto)phosphonates, $\beta$-keto-phosphoranylidines, phosphine oxides, $(C_6H_5)_3P=CHCOR_1$, $(CF_3-CH_2)_2POCH_2COR_1$ and the like. This transfers the $R_1$ containing substituent to the avermectin substrate and creates a 22,23-double bond. The reaction is carried out in an inert solvent such as a hydrocarbon, preferably toluene, or a $C_1$–$C_5$ alkanol such as methanol or ethanol, or other non-reactive solvents such as acetonitrile, at a temperature which can vary from a very cold dry ice bath ($-78°$ C.) to $100°$ C., or the reflux temperature of the reaction mixture. The reaction must be maintained in the dry state and all solvents must be water-free. The reaction mixture may also contain an alkali metal bis(trimethylsilyl)amide. The reaction is complete in from 5 minutes to 2 hours with the duration of the reaction dependent upon the nature of the particular $R_1$ group and the temperature of the reaction, with higher temperatures generally requiring shorter reaction times. The course of the reaction is conveniently followed by analyzing aliquots of the reaction mixture on thin layer chromatography (tlc) to determine the degree to which the reaction is completed. The tlc analysis can be used to determine if higher temperatures or longer reaction times are needed to complete the reaction. The products are isolated using techniques known to those skilled in the art.

Next, the double bond of Compound IV is reduced to a single bond, Compound V. The reduction is carried out with any of a variety of reducing agents such as hydrogen in the presence of a heavy metal catalyst; magnesium metal in methanol; sodium dithionite and sodium bicarbonate in the presence of a phase transfer catalyst, in particular a tetraalkyl ammonium phase transfer catalyst, and the like. The reaction is generally carried out in a non-reducible solvent such as a loweralkanol, tetrahydrofuran and the like. The reaction is generally carried out at from $0°$ to $60°$ C., preferably at room temperature and is complete in from 5 minutes to 2 hours.

In the next step the keto group is reduced to a hydroxy group using standard reducing agents such as lithium aluminum hydride, sodium borohydride, oxazoborolidines, boranes and the like. The reaction is carried out in a non-reducible solvent such as ether, tetrahydrofuran, methanol, ethanol and the like at a temperature of from $-78°$ C. to room temperature and is complete in from 5 minutes to 1 hour. The hydroxy product compound VI may be isolated and purified using procedures known to those skilled in the art, however, generally the material may be used without further purification in the next step.

Additional derivatives can be generated from V wherein $R_1$=H. Nucleophilic addition of carbon nucleophiles to the aldehyde function of V can generate VI wherein the $R_1$ function is derived from alkyl (or aryl) Grignard, cuprate or lithium reagents.

Alternatively, treatment of aldehyde V, with a Lewis acid, such as boron trifluoride etherate, magnesium bromide etherate, or zinc iodide at low temperature, can induce cyclization to generate VII wherein $R_1$ is an alkoxy group. The alkoxy group at $C_{21}$ is transferred to the $C_{24}$ position during the transformation.

The cyclization step prepares the final product compound VII from the hydroxy compound VI. The reaction is carried out with a catalytic amount of a reagent formed from a mixture of pyridine and p-toluene sulfonic acid (pyridinium-p-toluene sulfonic acid or PPTS). The PPTS is generally formed as a 1:1 mixture of pyridine and p-toluene sulfonic acid although slight variations from the 1:1 ratio are acceptable. The PPTS is used in approximately 0.01% quantities relative to the avermectin compound and the reaction is carried out in any protic solvent such as methanol or ethanol or chlorinated hydrocarbons, such as methylene chloride or chloroform. The reaction is carried out at from room temperature to $60°$ C. and is generally complete in from 5 minutes to 10 hours. The products are isolated using techniques known to those skilled in the art.

The intermediate compound VI need not be isolated prior to the final step of the reaction, or compound VI can be isolated using only crude separation techniques prior to being cyclized in the final step of the reaction sequence. This has not been found to have had any adverse effects upon the efficiency of the cyclization step.

The foregoing series of reactions is carried out using protecting groups on the reactive functions, such as hydroxy groups, on the avermectin molecule. Following the cyclization step, the protecting groups may be removed to afford the unprotected final product. However, as is indicated in the above formula by asterisks, the final product contains at least two new asymmetric center, at carbons 21 and 24 which would result in a total of at least four stereoisomers for each product. Additional stereoisomers may result if R at the 23 position is other than hydrogen. The isomers can be readily separated from each other prior to the removal of the protecting groups using chromatographic techniques, such as column chromatography. If the protecting groups are removed, the separation of the isomer is still readily accomplished chromatographically using thin layer or preparative layer chromatography, or reverse phase high pressure liquid chromatography.

In addition, following the removal of the protecting groups the, C-21 epimeric compound can be treated with a lower alkanol, preferably a methanol solution of p-toluene sulfonic acid (tosic acid) which opens the 5-membered ring and closes it again asymmetrically creating an equilibrium with the oxygen of the 5-membered ring predominantly in the $\alpha$-position. The 24-position remains a mixture of epimers however, and such stereoisomers can be further separated using high pressure liquid chromatography. The mixtures of stereoisomers as well as the isolated stereoisomers have been found to have substantial activity as antiparasitic or insecticidal products.

Some additional substituents can be prepared on the instant compound using techniques known to those skilled in the art, such as the alkylthio or substituted alkylthio substitutents at the 4' and 4" positions and the oxidized derivatives thereof. The substitutents can be synthesized either prior to the preparation of the 6,5-spiroketal ring system or after the 6,5-spiroketal system is prepared. However, to avoid undesired side-reactions, in particular where the alkylthio group contains reactive substitutents, it is often preferred to prepare the 4' or 4" alkylthio substituent after the reactions for the preparation of the 6,5-spiroketal ring system have been completed.

The preparation of the 4' and 4" alkylthio compounds of this invention is best accomplished when the avermectin starting materials are protected at the 5-hydroxy position to avoid substitution at this position. With this position protected, the reactions may be carried out at the 4"- or 4'-positions without affecting the remainder of the molecule. The 5-hydroxy group is protected by a tert.-butyldimethylsilyl group before displacement at the 4"- or 4'-hydroxyl group has occurred. The 23-hydroxy group is less reactive and the 7-hydroxy group is very unreactive, and these need not be protected.

The preparation of the 4' and 4" alkylthio compounds requires that the avermectin starting materials are converted to nucleophilic displacement to derivatives with good leaving groups at the 4"- or 4'-position, preferably halo-or alkyl-substituted sulfonyl groups, more preferably trifluoromethanesulfonyl- or iodo- groups. Subsequently, these leaving groups are displaced by sulfur-containing nucleophiles to obtain the desired 4"-deoxy-4"-alkyl-thio avermectin derivatives, (which also may be modified further).

The 4"-or 4'-alkyl substituted sulfonyl intermediate is prepared from the 5-position protected avermectin using the appropriate sulfonic anhydride or the appropriate sulfonyl chloride in an inert solvent such as a chlorinated hydrocarbon, tetrahydrofuran, (THF) or ether, preferably methylene chloride, in the presence of base at $-15°$ to $10°$ C. over a period of 15 minutes to 1 hour. The 4" or 4'-alkyl substituted sulfonyl compound may be isolated using techniques known to those skilled in the art. Then the 4"-or 4' sulfonylavermectin is substituted at the 4"-or 4'-position by sulfur-containing nucleophiles. The reaction is carried out at or near at room temperature in an inert solvent such as dimethylformamide (DMF), dimethylsulfoxide (DMSO), THF, chlorinated hydrocarbons, or ether, preferably DMF, with the desired thiol nucleophile, either the metallic thiol or a thiol with a base such as potassium carbonate at $0°$ to $25°$ C. over a period of 1 to 4 hours. It has been found useful to include in the reaction mixture a small quantity of crown ethers such as 18-crown-6 (1,4,7,10,15,16-hexaoxacyclo octadecane) the presence of the crown ether facilitates the reaction and generally significantly reduces the duration of the reaction. The products are isolated using known techniques.

There are two possible epimers at the 4" or 4'-position: one with the stereo chemistry exactly as in the natural avermectins with an equatorial (or $\alpha$) substituent and one with the axial (or $\beta$) configuration. The latter is called 4"- or 4'-epi. The reaction with strong nucleophiles results predominantly in the product with the inverted configuration. The reaction with hard nucleophiles usually gives both compounds, which are separable, but since both possess high biological activities, they need not be separated. Both epimers are considered part of this invention, either separate or in a mixture.

Nucleophilic substitution of the leaving group can be also accomplished by iodine, by adding a halogen salt to a stirring solution of the avermectin substituted with a good leaving group at the 4"-position in DMF, DMSO, THF or a chlorinated hydrocarbon and allowing the reaction to stir at room temperature from 1 to 6 hours. The product is isolated using known techniques. The 4"-halogen atom can, in turn, be displaced by other nucleophiles, including other sulfur-containing nucleophiles.

In addition, the sulfur-containing 4"-substituent can be further modified. Oxidation of the 4"-sulfur in an unreactive solvent such as methylene chloride with an oxidating agent such as m-chloroperbenzic acid at $-15°$ to $25°$ C. for a period of 30 minutes to 2 hours gives the sulfoxide and the sulfone. Both enantiomers of the sulfoxide are obtained.

The sulfur-containing 4'-and 4" groups can be oxidized to the corresponding sulfoxy and sulfonyl groups in a solvent such as a chlorinated hydrocarbon, THF, ether, or lower alcohol, preferably, methylene chloride. An oxidizing agent such as a peracid, preferably m-chloroperbenzoic acid, is added to a solution of the 4"- or 4'-substituted avermectin. By varying the temperature (from $-30°$ C. to room temperature) and the number of equivalents of oxidizing agent, the relative yields of the sulfoxide and sulfone can be controlled. The products are separated and isolated using techniques known to those skilled in the art.

Further modifications of the side chain can be accomplished when a thio-alcohol is used as the nucleophile. The hydroxyl group of the alcohol on the sulfur-containing side chain can undergo any the reactions and chemistry that is possible at the 4"-or 4'-hydroxy group, including, but not limited to, those described herein.

Following the desired substitution and modification at the 4"-position, the 5-hydroxy group is deprotected, and, if desired, modifications of the molecule at the 5-position can occur.

The foregoing reactions carried out at the 4"-position of the avermectin can be carried out at the 4'-position of the avermectin monosacchoride to affect the correspondingly substituted monosacchoride derivatives.

The preparation of additional derivatives of the various reactive substituents can also be carried out using procedures well known to those skilled in the art. See for example U.S. Pat. No. 4,906.619 to Eskola et al, for the preparation of various alkylated avermectins; U.S. Pat. No. 4,427,663 to Mrozik for the preparation of various 4' or 4" keto or amino derivatives; U.S. Pat. No. 4,201,861 to Mrozik et al, for the preparation of various, acylated avermectins: U.S. Patents Re 32006 and RE 32034 to Chabala et al for the preparation of various 13 substituted avermectins; U.S. Pat. No. 4,200,981 to Fisher et al for the preparation of various 5-alkylated compounds; and U.S. Pat. No. 4,895,837 to Mrozik food a discussion of various procedures for the protection of avermectin compounds.

The instant compounds are potent endo- and ecto-antiparasitic agents against parasites particularly helminths, ectoparasites, insects, and acarides, infecting man, animals and plants, thus having utility in human and animal health, agriculture and pest control in household and commercial areas.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats, fish, buffalo, camels, llamas, reindeer, laboratory animals, furbearing animals, zoo animals and exotic species and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Habronema, Druschia, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The compounds of this invention have unexpectedly high activity against these parasites, and in addition are also active against Dirofilaria in dogs and cats, Nematospiroides, Syphacia, Aspiculuris in rodents, arthropod ectoparasites of animals and birds such as ticks, mites, lice, fleas, blowflies, in sheep Lucilia sp., biting insects and such migrating diperous larvae as Hypoderma sp. cattle, Gastrophilus in horses, and Cuterebra sp. in rodents and nuisance flies including blood feeding flies and filth flies.

The instant compounds are also useful against parasites which infect humans. The most common genera of parasites of the gastro-intestinal tract of man are Ancylostoma, Necator, Ascaris, Stronyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunuculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., the housefly Musca domestica as well as fleas, house dust mites, termites and ants.

The compounds are also useful against insect pests of stored grains such as Tribolium sp., Tenebrio sp. and of agricultural plants such as aphids, (Acyrthiosiphon sp.); against migratory orthopterans such as locusts and immature stages of insects living on plant tissue. The compounds are useful as a nematocide for the control of soil nematodes and plant parasites such as Meloidogyne sp. which may be of importance in agriculture. The compounds are also highly useful in treating acerage infested with fire ant nests. The compounds are scattered above the infested area in low levels in bait formulations which are brought back to the nest. In addition to a direct-but-slow onset toxic effect on the fire ants, the compound has a long-term effect on the nest by sterilizing the queen which effectively destroys the nest.

The compounds of this invention may be administered in formulations wherein the active compound is intimately admixed with one or more inert ingredients and optionally including one or more additional active ingredients. The compounds may be used in any composition known to those skilled in the art for administration to humans and animals, for application to plants and for premise and area application to control household pests in either a residential or commercial setting. For application to humans and animals to control internal and external parasites, oral formulations, in solid or liquid or parenteral liquid, implant or depot injection forms may be used. For topical application dip, spray, powder, dust, pour-on, spot-on, jetting fluid, shampoos, collar, tag or harness, may be used. For agricultural premise or area application, liquid spray, powders, dust, or bait forms may be used. In addition "feed-through" forms may be used to control nuisance flies that feed or breed in animal waste. The compounds are formulated, such as by encapsulation, to lease a residue of active agent in the animal waste which controls filth flies or other arthropod pests.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the instant compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents, and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets or liquid which may then be added to the finished feed or optionally fed separately. Alternatively, feed based individual dosage forms may be used such as a chewable treat. Alternatively, the antiparasitic compounds of this invention may be administered to animals parenterally, for example, by intraruminal, intramuscular, intravascular, intratracheal, or subcutaneous injection in which the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, propylene glycol, and aqueous parenteral formulations are also used. The active compound or compounds are dissolved or suspended in the parenteral formulation for administration; such formulations generally contain from 0.0005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting arthropods in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1-5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.005 to 2.0% weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular compound employed, the compounds of this invention are usually fed at concentrations of between 0.00001 to 0.002% in the feed in order to achieve the desired anti-parasitic result.

In using the compounds of this invention, the individual compounds may be prepared and used in that form. Alternatively, mixtures of the individual compounds may be used, or other active compounds not related to the compounds of this invention.

The compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The following examples are provided in order that this invention might be more fully understood; they are not to be construed as limitative of the invention.

EXAMPLE 1

4'',5-Di-O-t-Butyldimethylsilyl-Avermectin B2a

To a solution of 58.2 g (65 mmol) of dried avermectin B2a in 400 mL of sieve-dried dimethylformamide and 30 mL of freshly distilled triethylamine was added a solution of 29.8 g (198 mmol, 3 equiv.) of t-butyldimethylsilyl chloride in 200 mL of dichloromethane. The mixture was stirred at room temperature 16 hours then poured into ice water and extracted with dichloromethane. The organic phases were combined and washed with water, brine, and dried over magnesium sulfate. Evaporation of the solvent afforded an oil which was purified by silica gel liquid chromatography using 20% ethyl acetate-hexanes to yield 34.2 g of 4'',5-di-O-t-butyldimethylsilyl-avermectin B2a characterized by its NMR and mass spectra.

EXAMPLE 2

4'',5-Di-O-t-Butyldimethylsilyl-23-oxo-Avermectin B2a

A 5-L 3-neck flask equipped with a thermometer, mechanical stirrer, and dropping funnel was charged with 400 mL of dichloromethane and 16 mL (0.185 mol) of oxalyl chloride. The solution was cooled to $-70°$ C., under nitrogen while a solution of 25 mL (0.350 mol) of dimethylsulfoxide in 200 mL of dichloromethane was added dropwise over 30 minutes keeping the internal temperature below $-65°$ C. The mixture was stirred at $-70°$ C. for 1 hour. A solution of 114.75 g (0.103 mmol) of 4'',5-di-O-t-butyldimethylsilyl-avermectin B2a in 900 mL of dichloromethane was then added dropwise over 45 minutes keeping the temperature of the mixture below $-65°$ C. After an additional 2 hours at $-70°$ C., 115 mL of triethylamine was added dropwise over 10 minutes again keeping the temperature below $-65°$ C. The reaction was then stirred at approximately $10°$ C. for 1 hour before the solvent was removed in vacuo. The residue was taken up in 1.5 L of ether and washed with 500 mL of water. The aqueous layer was extracted with 500 mL of ether. The combined ether layers were washed sequentially with $2 \times 1$ L of water, 1 L of saturated sodium bicarbonate, and 1 L of brine, then dried over magnesium sulfate. The solvent was removed to afford 100 g of yellow foam purified by column chromatography (4 kg silica gel, eluted with 5–25% ethyl acetatehexane eluant). The product was obtained as a yellow foam (101 g, 88% yield). NMR (300 MHz, TMS) $\delta 0.08$ (d, J=6 Hz), 0.14 (s), 0.9 (s), 0.93 (s), 0.98 (m), 1.16 (d, J=7 Hz), 1.2 (d, J=Hz), 1.24 (d, J=7 Hz), 1.45 (s), 1.5 (m), 1.8 (s), 2.22 (m), 2.44 (m), 3.12 (t, J=9 Hz), 3.2 (t, J=9 Hz), 3.32 (s), 3.42 (s), 3.6 (m), 3.81 (d, J=6 Hz), 3.93 (s), 3.98 (sh s), 4.44 (d, J=6 Hz), 4.62 (dq, J=2,14 Hz), 4.74 (d, J=3 Hz), 4.93 (t, J=7 Hz), 5.3 (m), 5.7 (m), 5.8 (m); mass spec: FAB 1123 (M+Li).

EXAMPLE 3

4'',5-Di-O-t-Butyldimethylsilyl-7-O-trimethylsilyl-23-O-trimethylsilyloxy-Avermectin B1a To a solution of 101 mg (0.09 mmol) of 4'',5-di-O-t-butyldimethylsilyl-23-oxo-avermectin B2a in 2 mL of distilled tetrahydrofuran at $-78°$ C. was added 0.400 mL of a 1.0M solution of lithium bis(trimethylsilyl)amide in a mixture of hexanes. The mixture was stirred at −78° C., under argon, for 1 hour before 0.20 mL of the supernatant of a centrifuged 1:3 mixture of triethylamine and trimethylchlorosilane was added dropwise via a syringe. After another 30 minutes, 2 ml of a saturated aqueous sodium bicarbonate solution was added and the mixture was allowed to warm to room temperature. The reaction mixture was then partitioned between water and ether and the ethereal extracts were combined and dried over magnesium sulfate. Filtration and evaporation of the ther afforded 120 mg of 4",5-di-O-t-butyldimethylsilyl-7-O-trimethylsilyl-23-O-trimethylsilyloxy-avermectin B1a characterized by its NMR δ0.08 (d, J=6 Hz), 0.12 (s), 0.18 (s), 0.88 (s), 0.92 (s), 1.18 (d, J=8 Hz), 1.23 (d, J=8 Hz), 1.26 (d, J=8 Hz), 1.5 (s), 1.51 (m), 1.78 (s), 2.3 (m), 2.58 (m), 3.12 (t, J=9 Hz), 3.22 (t, J=9 Hz), 3.25 (s), 3.32 (s), 3.4 (s), 3.8 (d, J=6 Hz), 3.82 (m), 3.98 (s), 4.39 (d, J=4 Hz), 4.6 (q, J=16 Hz), 4.68 (sh d, J=2 Hz, C22H), 4.8 (d, J=3 Hz), 4.9 (m), 5.1 (m), 5.25 (d, J=3 Hz), 5.45 (s), 5.7 (m).

EXAMPLE 4

4",5-Di-O-t-Butyldimethylsilyl-7-O-trimethylsilyl-22-hydroxy-23-oxo-Avermectin B2a To a solution of 135 mg (0.107 mmol) of 4",5-Di-O-t-butyldimethylsilyl-7-O-trimethylsilyl-23-O-trimethylsilyloxy-Avermectin B1a in 2 mL of dichloromethane was added a solution of 21 mg (0.12 mmol) of m-chloroperbenzoic acid in 1 mL of dichloromethane in one portion. After 20 minutes at 20° C., 0.2 mL of dimethylsulfide was added. The mixture was stirred another 30 minutes before the addition of aqueous sodium bicarbonate and extraction with ethyl acetate. The combined organic fractions were dried, filtered, and evaporated to afford 150 mg of solid. This product mixture was separated by preparative thin layer chromatography (20% ethyl actate-hexane) to afford 40 mg of 4",5-Di-O-t-butyldimethylsilyl-7-O-trimethylsilyl-22-hydroxy-23-oxo-Avermectin B2a. NMR δ0.08 (d, J=6 Hz), 0.14 (s), 0.88 (s), 0.92 (s), 0.96 (d, J=6 Hz), 0.98 (d, J=6 Hz), 1.16 (d, J=7 Hz), 1.20 (d, J=6 Hz), 1.23 (d, J=6 Hz), 1.43 (s), 1.50 (s), 1.52 (m), 1.78 (s), 2.24 (m), 2.4 (dd, J=6,12 Hz), 2.58 (m), 3.12 (t, J=9 Hz), 3.22 (t, J=9 Hz), 3.3 (s), 3.32 (s), 3.4 (s), 3.62 (m), 3.82 (m), 3.82 (d, J=6 Hz), 3.92 (d, J=7 Hz), 3.97 (s), 4.38 (d, J=3 Hz), 4.6 (q, J=15 Hz), 4.77 (d, J=3 Hz), 4.83 (m), 5.05 (br d, J=7 Hz), 5.25 (d, J=3 Hz), 5.5 (s), 5.7 (m); mass spec. FAB 1212 (M+Li+H).

EXAMPLE 5

Preparation of aldehyde-acid

To a solution of 600 mg (0.5 mmol) of 4",5-Di-O-t-butyldimethylsilyl-7-O-trimethylsilyl-22-hydroxy-23-oxo-Avermectin B2a in 6 mL of benzene in an aluminum foil-covered glass vial was added 400 mg (0.9 mmol) of lead tetraacetate in one portion. After 30 minutes at 20° C., the solution was poured into a separatory funnel containing 12 mL of water and 600 mg of sodium sulfite. The mixture was then shaken and extracted with ethyl acetate. The combined extracts were dried (MgSO4), filtered, and evaporated to afford 600 mg of solid. Flash chromatography through a column of silica gel eluting with 2:1 hexane:ethyl acetate, then acetone afforded 250 mg of starting material and 230 mg of aldehyde-acid. NMR δ0.08 (d, J=6 Hz), 0.13 (s), 0.89 (s), 0.92 (s), 1.15 (d, J=6 Hz), 1.18 (d, J=6 Hz), 1.20 (d, J=6 Hz), 1.26 (d, J=6 Hz), 1.5 (s), 1.53 (m), 1.78 (s), 2.3 (m), 2.78 (br s), 3.13 (t, J=9 Hz), 3.23 (t, J=9 Hz), 3.23 (s), 3.32 (s), 3.36 (m), 3.42 (br s), 3.68 (m), 3.81 (m), 3.82 (d, J=6 Hz), 3.98 (s), 4.38 (s), 4.6 (q, J=15 Hz), 4.79 (d, J=2 Hz), 4.86 (br s), 5.12 (br s), 5.3 (s), 5.44 (s), 5.7 (m).

EXAMPLE 6

Transketalization of Aldehyde-acid to Methoxy Aldehyde (III) and 2R,3R,4S-2,4-dimethyl-3-hydroxyhexanoic acid To a solution of 8 g of pyridinium tosylate in 80 mL of dry methanol was added 16.3 g of the aldehyde-acid from Example 5. The mixture was stirred at 20° C. for 1.5 hours before 4 mL of triethylamine was added. The mixture was then transferred to a separatory funnel containing 4.4 g of sodium bicarbonate and 500 mL of water. The mixture was extracted with ether and the aqueous layer was then acidified with 2N HCl and extracted with ethyl acetate to recover 1.6 g of 2R,3R,4S-2,4-dimethyl-3-hydroxyhexanoic acid as an amber oil. The ether extracts were combined and dried over magnesium sulfate. Filtration and evaporation of the solvent afforded 15.5 g of solid as a 1:1:1 mixture of methoxy ketals and the aldehyde-acid in addition to some minor products with a slower Rf than the methoxy ketal but faster than the aldehyde-acid. The mixture was separated by flash column chromatography on 550 g of silica gel eluted with 3:1 and then 2:1 hexane: ethyl acetate to yield 5.1 g and 4.0 g and 3.9 g of the methoxy ketals each characterized by NMR and mass spectroscopy. NMR of methoxy-ketal A: δ0.08 (d, J=6 Hz), 0.12 (s), 0.14 (s), 0.88 (s), 0.92 (s), 1.17 (d, J=7 Hz), 1.21 (d, J=7 Hz), 1.25 (d, J=7 Hz), 1.5 (m), 1.51 (s), 1.78 (s), 2.3 (m), 2.5 (m), 3.13 (t, J=9 Hz), 3.22 (t, J=9 Hz), 3.28 (sh d, J=2 Hz), 3.32 (s), 3.38 (s), 3.44 (s), 3.65 (m), 3.82 (d, J=6 Hz), 3.98 (s), 4.38 (d, J=3 Hz), 4.6 (dq, J=2,15 Hz), 4.7 (m), 4.78 (d, J=3 Hz), 5.12 (d, J=11 hz), 5.30 (d, J=3 Hz), 5.48 (s), 5.57 (m), 5.75 (dd, J=11, 16 Hz), 9.37 (s). NMR of methoxy ketal B: δ0.08 (d, J=6 hz), 0.13 (s), 0.88 (s), 0.90 (m), 0.92 (s), 1.18 (d, J=7 Hz), 1.21 (d, J=7 Ha), 1.26 (d, J=6 Hz), 1.42 (s), 1.5 (m), 1.52 (s), 1.6 (m), 1.78 (s), 1.90 (d, J=12 Hz), 2.35 (m), 2.58 (tt, J=6, 2 Hz), 3.13 (t, J=9 Hz), 3.22 (t, J=9 Hz), 3.25 (s), 3.28 (s), 3.32 (s), 3.43 (s), 3.66 (m), 3.82 (d, J=6 Hz), 3.84 (m), 3.99 (s), 4.38 (d, J=3 Hz), 4.60 (dq, J=2, 15 Hz), 4.80 (d, J=3 Hz), 4.90 (m), 5.15 (dd, J=5, 12 Hz), 5.29 (d, J=3 Hz), 5.46 (s), 5.57 (m, J=9 Hz), 5.63 (d, J=12 Hz), 5.76 (dd, J=12, 15 Hz), 9.39 (s). The stereochemical assignment at C21 for the methoxy ketal isomers A and B was based on the nonreversible conversion of A to B when each pure isomer was resubjected to acidic methanol. Isomer B being the thermodynamically stable isomer has been assigned the axial methoxy/equitorial formyl configuration. The chiral acid was esterified with excess diazomethane and purified by flash chromatography with 15% ethyl acetate-hexane to yield 1 g of methyl ester $[\alpha]_D = -9.5°$, c=8.9 g/dL dichloromethane, characterized by its NMR spectrum.

EXAMPLE 7

Preparation of 4",5-Di-O-t-butyldimethylsilyl-21-O-3-(methyl 2R,3R,4S-2,4-dimethylhexanoate)-22-oxo-21,25-seco-7-O-trimethylsilyl-Avermectin 24.75 g Hydroxy ketone II (20.54 mmol) was dissolved in 125 mL dry methanol at 0° C. To this was added sequentially 9.1 mL pyridine followed by 9.1 g lead tetraacetate (added over five minutes in 1 g portions). The reaction was stirred at 0° C. then at room temperature for 10 minutes. The solution was then poured into 125 mL saturated Na₂S₂O₄, extracted with ethyl acetate, the organic layer washed with brine and dried with magnesium sulfate. The magnesium sulfate was filtered off and the solvent was removed in vacuo. The resultant oil was purified by flash chromatography on silica gel with 85:15 hexanes:acetone as eluant to yield 23.2 g (91%) of the title compound which was characterized by NMR.

EXAMPLE 8

Preparation of Methoxy-aldehyde III

To 8 g pyridinium p-toluenesulfonate in 80 mL methanol at RT was added 8.9 g 4",5-di-O-t-butyldimethylsilyl-21-O-3-(methyl 2R,3R,4S-2,4-dimethylhexanoate)-22-oxo-21,25-seco-7-O-trimethylsilyl-Avermectin (7.21 mmol) and the reaction was stirred for 1 hour. The solution was diluted with 100 mL ethyl acetate, washed with 100 mL saturated sodium bicarbonate, then brine and then the organic layer was dried with magnesium sulfate. The magnesium sulfate was filtered off, and the solvent removed in vacuo. The methoxy aldehyde III was obtained in pure form after flash chromatography on silica gel with 85:15 hexanes:acetone as eluant and was characterized by NMR.

EXAMPLE 9

Preparation of 4",5-DiO-t-butyldimethylsilyl-7-O-trimethylsilyl-21,25-seco-24-desmethyl-25-des(2-butyl)-21-methoxy-25-nor-24-oxo-Avermectin (IVa)

100 mg aldehyde III form Example 8 (97 μmol) and 64 mg Ph₃PCHCHO (106 μmol) were mixed in 2 ml toluene. The solution was refluxed for 15 min, cooled to room temperature, then purified directly by flash chromatography silica gel with 3:1 hexanes:ethyl acetate as eluant to yield 89 mg (88%) of the title compound which was characterized by NMR.

EXAMPLE 10

Preparation of 4",5-Di-O-t-butyldimethylsilyl-7-O-trimethylsilyl-21,25-seco-24-desmethyl-25-des(2-butyl)-21-methoxy-25-nor-24-oxo-24-methyl-Avermectin (IVb)

200 mg aldehyde III from Example 8 (196 μmol) and 134 mg Ph₃PCHCH(O)CH₃ (420 μmol) were placed in 3 mL toluene and heated to reflux for 20 min. The reaction was cooled to 0° C., quenched with saturated sodium chloride and extracted with ethyl acetate. The organic layer was dried (magnesium sulfate), filtered and concentrated in vacuo. The crude was purified by flash chromatography on silica gel using 3:1 hexanes:ethyl acetate as eluant to afford 160 mg (77%) of the titled compound which was characterized by NMR.

EXAMPLE 11

Preparation of 4",5-Di-O-t-butyldimethylsilyl-7-O-trimethylsilyl-21,25-seco-24-desmethyl-25-des(2-butyl)-21-methoxy-25-nor-24-oxo-24-i-propyl-Avermectin (IVc)

200 mg aldehyde III (196 μmol) was placed in 5 mL acetonitrile at room temperature with 76 mg dimethyl (2-oxo-3-methylbutyl)phosphate (393 μmol) and 39 mg lithium chloride (929 μmol). To this was added 101 μL diisopropylethylamine (784 μmol) dropwise over one minute. The reaction was stirred at room temperature for 10 minutes, then poured into 2 mL saturated ammonium chloride, extracted with ethyl acetate, washed with brine, and the organic layer was dried over magnesium sulfate. The magnesium sulfate was filtered off and the solvent was removed in vacuo. The crude was purified by flash chromatography on silica gel with 2:1 hexanes:ethyl acetate as eluant to yield 201 mg (95%) of the title compound which was characterized by NMR.

EXAMPLE 12

Preparation of 4",5-Di-O-t-butyldimethylsilyl-7-O-trimethylsilyl-21,25-seco-24-desmethyl-25-des(2-butyl)-21-methoxy-25-nor-24-oxo-24-t-butyl-Avermectin (IVd)

Following the procedure in Example 11, 350 mg aldehyde III (342 μmol), 142 mg dimethyl (2-oxo-3,3-dimethylbutyl)phosphonate (685 μmol) and 57 mg lithium chloride (1.37 mmol) were placed in 4 mL acetonitrile to which was added 245 μL diisopropylethylamine (1.37 mmol) to yield 330 mg (87%) of the title compound which was characterized by NMR.

EXAMPLE 13

Preparation of 4",5-Di-O-t-butyldimethylsilyl-7-O-trimethylsilyl-21,25-seco-24-desmethyl-25-des(2-butyl)-21-methoxy-25-nor-24-oxo-24-cyclohexyl-Avermectin (IVe)

Following the procedure in Example 11, 250 mg aldehyde III (246 μmol), 115 mg dimethyl cyclohexylcarbonylmethyl phosphonate (490 μmol) and 52 mg lithium chloride (1.23 mmol) were placed in 4 mL acetonitrile to which was added 126 μL diisopropylethylamine (980 μmol) to yield 256 mg (93%) of the title compound which was characterized by NMR.

EXAMPLE 14

Preparation of 4",5-Di-O-t-butyldimethylsilyl-7-O-trimethylsilyl-21,25-seco-24-desmethyl-25-des(2-butyl)-21-methoxy-25-nor-24-methoxycarbonyl-Avermectin (IVf)

12 mg of bis(2,2,2-trifluoroethyl) (methoxycarbonylmethyl) phosphonate (54 μmol) was cooled to −78° C. in 2 mL toluene. 98 μL 0.5M potassium bis(trimethylsilyl)amide (49 μmol) was added and the reaction was stirred for 5 minutes. 50 mg aldehyde III (49 μmol) in 1 mL toluene was added in one portion. The reaction was stirred at −78° C. for 30 minutes then warmed to room temperature. The reaction was quenched with saturated ammonium chloride, extracted with ethyl acetate, and the organic layer was washed with brine and dried with magnesium sulfate. The magnesium sulfate was filtered and the solvent was removed in vacuo. The crude was purified by flash chromatography on silica gel with 3:1 hexanes:ethyl acetate as eluant to afford the title compound which was characterized by NMR.

EXAMPLE 15

Preparation of 4",5-Di-O-t-butyldimethylsilyl-7-O-trimethylsilyl-21,25-seco-24-desmethyl-25-des(2-butyl)-22,23-cis-21-methoxy-25-nor-24-methoxycarbonyl-Avermectin (IVf)

23 μL bis(2,2,2-trifluoroethyl) methoxycarbonylmethyl phosphonate (108 μmol) and 118 mg 18-crown-6 (490 μmol) were cooled to −78° C. in 5 mL toluene. To this was added dropwise 216 μL 0.5M potassium bis(- trimethylsilyl)amide (108 μmol). After 10 minutes, 100 mg aldehyde III (98 μmol) in 1 mL toluene was added in one portion. The reaction was stirred at −78° C. for 30 minutes, then warmed to room temperature. The reaction was quenched with 2 mL saturated ammonium chloride, extracted with ethyl acetate, the organic layer washed with brine and dried with magnesium sulfate. The magnesium sulfate was filtered off, the solvents removed in vacuo, and the crude purified by preparative layer chromatography (SiO$_2$) with 3:1 hexanes:ethyl acetate as eluant to yield 101 mg (96%) of the title compound which was characterized by NMR.

EXAMPLE 16

Preparation of
4″,5-Di-O-t-butyldimethylsilyl-7-O-trimethylsilyl-21,25-seco-24-desmethyl-25-des(2-butyl)-21-methoxy-25-nor-24-phenyl-Avermectin (IVg)

78 mg bis(2,2,2-trifluoroethyl) phenylcarbonylmethyl phosphonate (215 μmol) was placed in 5 mL toluene at −78° C. with 235 mg 18-crown-6 (979 μmol). 430 μL potassium bis(trimethylsilyl)amide (215 μmol) was added and the reaction stirred for 10 minutes. 200 mg aldehyde III (196 μmol) in 1 mL toluene was added dropwise and the reaction was stirred for 30 minutes at −78° C. and then 30 minutes at room temperature. The reaction was quenched with 3 mL saturated ammonium chloride, extracted with ethyl acetate, the organic layer was washed with brine and dried over magnesium sulfate. The magnesium sulfate was filtered off and the solvents removed in vacuo. The crude was purified by preparative layer chromatography with 4:1 hexanes:ethyl acetate as eluant to yield 173 mg (79%) of the title compound which was characterized by NMR.

EXAMPLE 17

Preparation of
4″,5-Di-O-t-butyldimethylsilyl-7-O-trimethylsilyl-21,25-seco-24-desmethyl-25-des(2-butyl)-21-methoxy-25-nor-24-oxo-24-(4-fluoro)phenyl-Avermectin (IVh)

Following the procedure in Example 11, 200 mg aldehyde III (196 μmol), 99 mg dimethyl (4-fluoro)phenylcarbonylmethyl phosphonate (402 μmol) and 40 mg lithium chloride (952 μmol) were placed in 4 mL acetonitrile to which was added 101 μL diisopropylethylamine (782 μmol) to yield 216 mg (95%) of the title compound which was characterized by NMR.

EXAMPLE 18

Preparation of
4″,5-Di-O-t-butyldimethylsilyl-7-O-trimethylsilyl-21,25-seco-24-desmethyl-25-des(2-butyl)-21-methoxy-25-nor-24-oxo-24-(4-methoxy)phenyl-Avermectin (IVi)

Following the procedure in Example 11, 200 mg aldehyde III (196 μmol), 105 mg dimethyl (4-methoxy)phenylcarbonylmethyl phosphonate (407 μmol) and 40 mg lithium chloride (952 μmol) were placed in 4 mL acetonitrile to which was added 101 μL diisopropylethylamine (782 μmol) to yield 197 mg (86%) of the title compound which was characterized by NMR.

EXAMPLE 19

Preparation of
4″,5-Di-O-t-butyldimethylsilyl-21,25-seco-24-desmethyl-25-des(2-butyl)-21-methoxy-25-nor-24-oxo-24-(2-furyl)-Avermectin (IVj)

Following the procedure in Example 11, 200 mg aldehyde III (210 μmol), 108 mg dimethyl (2-furyl)carbonylmethyl phosphonate (420 μmol) and 21 mg lithium chloride (980 μmol) were placed in 4 mL acetonitrile to which was added 72 μL diisopropylethylamine (420 μmol) to yield 173 mg (79%) of the title compound which was characterized by NMR.

EXAMPLE 20

Preparation of
4″,5-Di-O-t-butyldimethylsilyl-21,25-seco-24-desmethyl-25-des(2-butyl)-21-methoxy-25-nor-24-oxo-24-methoxymethyl-Avermectin (IVk)

Following the procedure in Example 11, 250 mg aldehyde III (246 μmol), 96 mg dimethyl (2-oxo-3-methoxypropyl) phosphonate (490 μmol) and 41 mg lithium chloride (980 μmol) were placed in 2.5 mL acetonitrile to which was added 175 μL diisopropylethylamine (980 μmol) to yield 270 mg (100%) of the title compound which was characterized by NMR.

EXAMPLE 21

Preparation of
4″,5-Di-O-t-butyldimethylsilyl-21,25-seco-24-desmethyl-25-des(2-butyl)-21-methoxy-25-nor-24-oxo-24-phenoxymethyl-Avermectin (IVl)

Following the procedure in Example 11, 200 mg aldehyde III (210 μmol), 108 mg dimethyl (2-oxo-3-phenoxypropyl)phosphonate (420 μmol) and 21 mg lithium chloride (980 μmol) were placed in 4 mL acetonitrile to which was added 72 μL diisopropylethylamine (420 μmol) to yield 191 mg (84%) of the title compound which was characterized by NMR.

EXAMPLE 22

Preparation of
4″,5-Di-O-t-butyldimethylsilyl-7-O-trimethylsilyl-21,25-seco-24-desmethyl-25-des(2-butyl)-21-methoxy-25-nor-24-oxo-24-triethylsiloxymethyl-Avermectin (IVm)

Following the procedure in Example 11, 200 mg aldehyde III (196 μmol), 116 mg dimethyl (2-oxo-3-(triethylsiloxy)propyl) phosphonate (392 μmol) and 17 mg lithium chloride (392 μmol) were placed in 4 mL acetonitrile to which was added 70 μL diisopropylethylamine (392 μmol) to yield 180 mg (77%) of the title compound which was characterized by NMR.

EXAMPLE 23

Preparation of
4″,5-di-O-t-butyldimethylsilyl-21-O-3-(methyl 2R,3R,4S-2,4-dimethylhexanoate)-24-oxo-21,25-seco-24-triethylsiloxymethyl-7-O-trimethylsilyl-Avermectin (IVn)

Following the procedure in Example 11, 247 mg methyl 4″,5-di-O-t-butyldimethylsilyl-21-O-3-(2R,3R,4S-2,4-dimethylhexanoate)-22-oxo-21,25-seco-7-O-trimethylsilyl-Avermectin (200 μmol), 118 mg dimethyl (2-oxo-3-(triethylsiloxy)propyl) phosphonate (400 μmol) and 17 mg lithium chloride (400 μmol) were placed in 4 mL acetonitrile to which was added 72 μL diisopropylethylamine (400 μmol) to yield 185 mg (66%) of the title compound which was characterized by NMR.

EXAMPLE 24

Preparation of
4'',5-Di-O-t-butyldimethylsilyl-7-O-trimethylsilyl-21,25-seco-24-desmethyl-25-des(2-butyl)-22,23-dihydro-21-methoxy-25-nor-24-oxo-Avermectin (Va)

350 mg IVa (334 μmol) was placed in 10 mL 1:1 benzene:water solution to which was added 506 mg sodium bicarbonate (6.02 mmol) and 100 mg Adogen 464. 523 mg sodium thiosulfate (3.0 mmol) was added and the solution heated to reflux for 15 minutes. The reaction was cooled to room temperature, extracted with ethyl acetate, the organic layer washed with brine and dried with magnesium sulfate. The magnesium sulfate was filtered off, the solvent removed in vacuo and the crude was purified by flash chromatography silica gel using 3:1 hexanes:ethyl acetate as eluant to yield 172 mg (82%) of the title compound which was characterized by NMR.

EXAMPLE 25

Preparation of
4'',5-Di-O-t-butyldimethylsilyl-7-O-trimethylsilyl-21,25-seco-24-desmethyl-25-des(2-butyl)-22,23-dihydro-21-methoxy-25-nor-24-oxo-24-methyl-Avermectin (Vb)

Following the procedure outlined in Example 24, 110 mg enone IVb (111 μmol) was reduced using 168 mg sodium bicarbonate (999 μmol), 50 mg Adogen 464, and 142 mg sodium thiosulfate in 5 mL 3:2 benzene:water to afford 90 mg (82%) of title compound which was characterized by NMR.

EXAMPLE 26

Preparation of
4'',5-Di-O-t-butyldimethylsilyl-7-O-trimethylsilyl-21,25-seco-24-desmethyl-25-des(2-butyl)-22,23-dihydro-21-methoxy-25-nor-24-oxo-24-i-propyl-Avermectin (Vc)

Following the procedure outlined in Example 24, 202 mg enone IVc (188 μmol) was reduced using 285 mg sodium bicarbonate (3.39 mmol), 50 mg Adogen 464, and 294 mg sodium thiosulfate (1.69 mmol) in 10 mL 1:1 benzene:water to afford 186 mg (92%) of the title compound which was characterized by NMR.

EXAMPLE 27

Preparation of
4'',5-Di-O-t-butyldimethylsilyl-7-O-trimethylsilyl-21,25-seco-24-desmethyl-25-des(2-butyl)-22,23-dihydro-21-methoxy-25-nor-24-oxo-24-t-butyl-Avermectin (Vd)

Following the procedure outlined in Example 24, 240 mg enone IVd (218 μmol) was reduced using 328 mg sodium bicarbonate (3.91 mmol), 50 mg Adogen 464, and 277 mg sodium thiosulfate (1.95 mmol) in 10 mL 1:1 benzene:water to afford 220 mg (91%) of the title compound which was characterized by NMR.

EXAMPLE 28

Preparation of
4'',5-Di-O-t-butyldimethylsilyl-7-O-trimethylsilyl-21,25-seco-24-desmethyl-25-des(2-butyl)-22,23-dihydro-21-methoxy-25-nor-24-oxo-24-cyclohexyl-Avermectin (Ve)

Following the procedure outlined in Example 24, 256 mg enone IVe (227 μmol) was reduced using 320 mg sodium bicarbonate (3.81 mmol), 50 mg Adogen 464, and 320 mg sodium thiosulfate (1.81 mmol) in 10 mL 1:1 benzene:water to afford 234 mg (91%) of the title compound which was characterized by NMR.

EXAMPLE 29

Preparation of
4'',5-Di-O-t-butyldimethylsilyl-7-O-trimethylsilyl-21,25-seco-24-desmethyl-25-des(2-butyl)-22,23-dihydro-21-methoxy-25-nor-24-methoxycarbonyl-Avermectin (Vf)

10 mg of enone IVf was placed in 1 mL methanol at room temperature to which was added 10 mg Mg°. The reaction was stirred for 45 minutes during which gas evolution was observed. The reaction was quenched with 3 mL saturated ammonium chloride, extracted with ethyl acetate, the organic layer washed with brine and dried over magnesium sulfate. The magnesium sulfate was filtered off, the solvent removed in vacuo and the crude purified by preparative layer chromatography with 3:1 hexanes:ethyl acetate as eluant to yield 8 mg (83%) of the title compound which was characterized by NMR.

EXAMPLE 30

Preparation of
4'',5-Di-O-t-butyldimethylsilyl-7-O-trimethylsilyl-21,25-seco-24-desmethyl-25-des(2-butyl)-22,23-dihydro-21-methoxy-25-nor-24-methoxycarbonyl-Avermectin (Vf)

Following the procedure outlined in Example 24, 160 mg enone IVf (150 μmol) was reduced using 226 mg sodium thiosulfate (2.7 mmol), 50 mg Adogen 464, and 239 mg sodium thiosulfate (1.35 mmol) in 10 mL 1:1 benzene:water to afford 107 mg (67%) of the title compound which was characterized by NMR.

EXAMPLE 31

Preparation of
4'',5-Di-O-t-butyldimethylsilyl-7-O-trimethylsilyl-21,25-seco-24-desmethyl-25-des(2-butyl)-22,23-dihydro-21-methoxy-25-nor-24-oxo-24-phenyl-Avermectin (Vg)

Following the procedure outlined in Example 24, 360 mg enone IVg (320 μmol) was reduced using 485 mg sodium bicarbonate (5.77 mmol), 50 mg Adogen 464, and 410 mg sodium thiosulfate (2.89 mmol) in 10 mL 1:1 benzene:water to afford 210 mg (58%) of the title compound which was characterized by NMR.

EXAMPLE 32

Preparation of
4″,5-Di-O-t-butyldimethylsilyl-7-O-trimethylsilyl-
21,25-seco-24-desmethyl-25-des(2-butyl)-22,23-dihy-
dro-21-methoxy-25-nor-24-oxo-24-(4-fluoro)phenyl-
Avermectin (Vh)

Following the procedure outlined in Example 24, 216 mg enone IVh (187 μmol) was reduced using 300 mg sodium bicarbonate (3.57 mmol), 50 mg Adogen 464, and 300 mg sodium thiosulfate (1.69 mmol) in 10 mL 1:1 benzene:water to afford 163 mg (75%) of the title compound which was characterized by NMR.

EXAMPLE 33

Preparation of
4″,5-Di-O-t-butyldimethylsilyl-7-O-trimethylsilyl-
21,25-seco-24-desmethyl-25-des(2-butyl)-22,23-dihy-
dro-21-methoxy-25-nor-24-oxo-24-(4-methoxy)phenyl-
Avermectin (Vi)

Following the procedure outlined in Example 24, 197 mg enone IVi (168 μmol) was reduced using 300 mg sodium bicarbonate (3.57 mmol), 50 mg Adogen 464, and 300 mg sodium thiosulfate (1.69 mmol) in 10 mL 1:1 benzene:water to afford 139 mg (71%) of the title compound which was characterized by NMR.

EXAMPLE 34

Preparation of
4″,5-Di-O-t-butyldimethylsilyl-7-O-trimethylsilyl-
21,25-seco-24-desmethyl-25-des(2-butyl)-22,23-dihy-
dro-21-methoxy-25-nor-24-oxo-24-(2-furyl)-Avermec-
tin (Vj)

Following the procedure outlined in Example 24, 130 mg enone IVj (125 μmol) was reduced using 189 mg sodium bicarbonate (2.25 mmol), 50 mg Adogen 464, and 160 mg sodium thiosulfate (1.13 mmol) in 10 mL 1:1 benzene:water to afford 50 mg (40%) of the titled compound which was characterized by NMR.

EXAMPLE 35

Preparation of
4″,5-Di-O-t-butyldimethylsilyl-7-O-trimethylsilyl-
21,25-seco-24-desmethyl-25-des(2-butyl)-22,23-dihy-
dro-21-methoxy-25-nor-24-oxo-24-methoxymethyl-
Avermectin (Vk)

Following the procedure outlined in Example 24, 270 mg enone IVk (247 μmol) was reduced using 374 mg sodium bicarbonate (4.45 mmol), 50 mg Adogen 464, and 316 mg sodium thiosulfate (2.22 mmol) in 10 mL 1:1 benzene:water to afford 210 mg (78%) of the title compound which was characterized by NMR.

EXAMPLE 36

Preparation of
4″,5-Di-O-t-butyldimethylsilyl-7-O-trimethylsilyl-
21,25-seco-24-desmethyl-25-des(2-butyl)-22,23-dihy-
dro-21-methoxy-25-nor-24-oxo-24-phenoxymethyl-
Avermectin (Vl)

Following the procedure outlined in Example 24, 120 mg enone IVl (104 μmol) was reduced using 157 mg sodium bicarbonate (1.87 mmol), 50 mg Adogen 464, and 133 mg sodium thiosulfate (937 μmol) in 10 mL 1:1 benzene:water to afford 50 mg (43%) of the title compound which was characterized by NMR.

EXAMPLE 37

Preparation of
4″,5-Di-O-t-butyldimethylsilyl-7-O-trimethylsilyl-
21,25-seco-24-desmethyl-25-des(2-butyl)-22,23-dihy-
dro-21-methoxy-25-nor-24-oxo-24-triethylsiloxymeth-
yl-Avermectin (Vm)

Following the procedure outlined in Example 24, 180 mg enone IVm (151 μmol) was reduced using 228 mg sodium bicarbonate (2.72 mmol), 50 mg Adogen 464, and 193 mg sodium thiosulfate (1.36 μmol) in 10 mL 1:1 benzene:water to afford 75 mg (42%) of the title compound which was characterized by NMR.

EXAMPLE 38

Preparation of Methyl
4″,5-di-O-t-butyldimethylsilyl-22,23-dihydro-21-O-3-
(2R,3R,4S-2,4-dimethylhexanoate)-25-nor-24-oxo-
21,25-seco-24-triethylsiloxymethyl-7-O-trimethylsilyl-
Avermectin (Vn)

Following the procedure outlined in Example 24, 180 mg enone IVn (128 μmol) was reduced using 194 mg sodium bicarbonate (2.31 mmol), 50 mg Adogen 464, and 163 mg sodium thiosulfate (1.15 μmol) in 10 mL 1:1 benzene:water to afford 130 mg (72%) of the title compound which was characterized by NMR.

EXAMPLE 39

Preparation of
4″,5-Di-O-t-butyldimethylsilyl-7-O-trimethylsilyl-24-
desmethyl-25-des(2-butyl)-22,23-dihydro-25-nor-Aver-
mectin (VIIa)

50 mg aldehyde Va (44 μmol) was placed in 3 mL methanol at 0° C. to which was added 50 mg sodium borohydride. After 10 minutes at 0° C., the reaction was quenched with saturated ammonium chloride and extracted with ethyl acetate. The organic layer was washed with brine, dried (magnesium sulfate), filtered and concentrated in vacuo. The crude product was dissolved in 3 mL methylene chloride at room temperature to which was added 5 mg pyridinium p-toluenesulfonate. The reaction was stirred for 1 hr, quenched with 300 μL of triethylamine and concentrated in vacuo. The crude was purified by flash chromatography on $SiO_2$ using 3:1 hexanes:ethyl acetate as eluant to yield 44 mg (92%) of the title compound which was characterized by NMR.

EXAMPLE 40

Preparation of
4″,5-Di-O-t-butyldimethylsilyl-7-O-trimethylsilyl-24-
desmethyl-25-des(2-butyl)-22,23-dihydro-24-methyl-25-
nor-Avermectin (VIIb)

Following the procedure outlined in Example 33, 130 mg ketone Vb (131 μmol) in 5 mL methanol was reduced with 50 mg sodium borohydride. The crude product was subsequently cyclized in 4 mL methylene chloride containing 5 mg pyridinium p-toluenesulfonate for 1 hr to yield 112 mg (89%) of the title compound which was characterized by NMR.

EXAMPLE 41

Preparation of
4'',5-Di-O-t-butyldimethylsilyl-7-O-trimethylsilyl-24-desmethyl-25-des(2-butyl)-22,23-dihydro-25-nor-24-i-propyl-Avermectin (VIIc)

Following the procedure outlined in Example 39, 186 mg ketone Vc (173 μmol) in 5 mL methanol was reduced with 120 mg sodium borohydride. The crude product was subsequently cyclized in 4 mL methylene chloride containing 5 mg pyridinium p-toluenesulfonate for 1 hr to yield 150 mg (82%) of the title compound which was characterized by NMR.

EXAMPLE 42

Preparation of
4'',5-Di-O-t-butyldimethylsilyl-7-O-trimethylsilyl-24-desmethyl-25-des(2-butyl)-22,23-dihydro-25nor-24-t-butyl-Avermectin (VIId)

Following the procedure outlined in Example 39, 330 mg ketone Vd (298 μmol) in 6 mL methanol was reduced with 50 mg sodium borohydride. The crude product was subsequently cyclized in 4 mL methylene chloride containing 5 mg pyridinium p-toluenesulfonate for 1 hr to yield 302 mg (94%) of the title compound which was characterized by NMR.

EXAMPLE 43

Preparation of
4'',5-Di-O-t-butyldimethylsilyl-7-O-trimethylsilyl-24-desmethyl-25-des(2-butyl)-22,23-dihydro-25-nor-24-cyclohexyl-Avermectin (VIIe)

Following the procedure outlined in Example 39, 234 mg ketone Ve (207 μmol) in 5 mL methanol was reduced with 100 mg sodium borohydride. The crude product was subsequently cyclized in 4 mL methylene chloride containing 5 mg pyridinium p-toluenesulfonate for 2 hours to yield 207 mg (91%) of the title compound which was characterized by NMR.

EXAMPLE 44

Preparation of
4'',5-Di-O-t-butyldimethylsilyl-7-O-trimethylsilyl-24-desmethyl-25-des(2-butyl)-22,23-dihydro-25-nor-24-methoxy-Avermectin (VIIf)

100 mg aldehyde Vf (103 μmol) was placed in 4 mL methylene chloride at $-78°$ C. 4 μL freshly distilled $BF_3 \cdot OMe_2$ was added. The reaction was quenched with 1 mL saturated ammonium chloride after 10 minutes at $-78°$ C., extracted with ethyl acetate, washed with brine, and the organic layer dried over magnesium sulfate. The magnesium sulfate was filtered off and the solvent was removed in vacuo. The crude was purified by preparative silica gel chromatography using 2:1 hexanes:ethyl acetate as eluant to yield 80 mg (78%) of the title compound which was characterized by NMR.

EXAMPLE 45

Preparation of
4'',5-Di-O-t-butyldimethylsilyl-7-O-trimethylsilyl-24-desmethyl-25-des(2-butyl)-22,23-dihydro-25-nor-24-phenyl-Avermectin (VIIg)

Following the procedure outlined in Example 39, 210 mg ketone Vg (187 μmol) in 6 mL methanol was reduced with 50 mg sodium borohydride. The crude product was subsequently cyclized in 4 mL methylene chloride containing 5 mg pyridinium p-toluenesulfonate for 1 hour to yield 181 mg (89%) of the title compound which was characterized by NMR.

EXAMPLE 46

Preparation of
4'',5-Di-O-t-butyldimethylsilyl-7-O-trimethylsilyl-24-desmethyl-25-des(2-butyl)-22,23-dihydro-25-nor-24-(4-fluoro)phenyl-Avermectin (VIIh)

Following the procedure outlined in Example 39, 163 mg ketone Vh (141 μmol) in 6 mL methanol was reduced with 120 mg sodium borohydride. The crude product was subsequently cyclized in 4 mL methylene chloride containing 5 mg pyridinium p-toluenesulfonate for 2 hours to yield 101 mg (63%) of the title compound which was characterized by NMR.

EXAMPLE 47

Preparation of
4'',5-Di-O-t-butyldimethylsilyl-7-O-trimethylsilyl-24-desmethyl-25-des(2-butyl)-22,23-dihydro-25-nor-24-(4-methoxy)phenyl-Avermectin (VIIi)

Following the procedure outlined in Example 39, 139 mg ketone Vi (119 μmol) in 5 mL methanol was reduced with 120 mg sodium borohydride. The crude product was subsequently cyclized in 4 mL methylene chloride containing 5 mg pyridinium p-toluenesulfonate for 1 hr to yield 102 mg (64%) of the title compound which was characterized by NMR.

EXAMPLE 48

Preparation of
4'',5-Di-O-t-butyldimethylsilyl-7-O-trimethylsilyl-24-desmethyl-25-des(2-butyl)-22,23-dihydro-25-nor-24-(2-furyl)-Avermectin (VIIj)

Following the procedure outlined in Example 39, 63 mg ketone Vj (60 μmol) in 5 mL methanol was reduced with 50 mg sodium borohydride. The crude product was subsequently cyclized in 4 mL methylene chloride containing 5 mg pyridinium p-toluenesulfonate for 1 hour to yield 50 mg (81%) of the title compound which was characterized by NMR.

EXAMPLE 49

Preparation of
4'',5-Di-O-t-butyldimethylsilyl-7-O-trimethylsilyl-24-desmethyl-25-des(2-butyl)-22,23-dihydro-25-nor-24-methoxymethyl-Avermectin (VIIk)

Following the procedure outlined in Example 39, 210 mg ketone Vk (180 μmol) in 5 mL methanol was reduced with 50 mg sodium borohydride. The crude product was subsequently cyclized in 4 mL methylene chloride containing 5 mg pyridinium p-toluenesulfonate for 1 hour to yield 192 mg (94%) of the title compound which was characterized by NMR.

EXAMPLE 50

Preparation of
4'',5-Di-O-t-butyldimethylsilyl-7-O-trimethylsilyl-24-desmethyl-25-des(2-butyl)-22,23-dihydro-25-nor-24-phenoxymethyl-Avermectin (VIIl)

Following the procedure outlined in Example 39, 60 mg ketone Vl (52 μmol) in 5 mL methanol was reduced with 50 mg sodium borohydride. The crude product was subsequently cyclized in 4 mL methylene chloride containing 5 mg pyridinium p-toluenesulfonate for 1 hour to yield 50 mg (85%) of the title compound which was characterized by NMR.

EXAMPLE 51

Preparation of
4",5-Di-O-t-butyldimethylsilyl-7-O-trimethylsilyl-24-desmethyl-25-des(2-butyl)-22,23-dihydro-25-nor-24-triethylsiloxymethyl-Avermectin (VIIm)

Following the procedure outlined in Example 39, 75 mg ketone Vm (53 μmol) in 5 mL methanol was reduced with 50 mg sodium borohydride. The crude product was subsequently cyclized in 4 mL methylene chloride containing 5 mg pyridinium p-toluenesulfonate for 1 hour to yield 60 mg (82%) of the title compound which was characterized by NMR.

EXAMPLE 52

Preparation of
4",5-Di-O-t-butyldimethylsilyl-7-O-trimethylsilyl-24-desmethyl-25-des(2-butyl)-22,23-dihydro-25-nor-24-triethylsiloxymethyl-Avermectin (VIIm)

Following the procedure outlined in Example 39, 130 mg ketone Vn (93 μmol) in 5 mL methanol was reduced with 50 mg sodium borohydride. The crude product was subsequently cyclized in 4 mL methylene chloride containing 5 mg pyridinium p-toluenesulfonate for 5 minutes to yield 121 mg (95%) of the title compound which was characterized by NMR.

EXAMPLE 53

Preparation of
4",5-Di-O-t-butyldimethylsilyl-7-O-trimethylsilyl-24-desmethyl-25-des(2-butyl)-22,23-dihydro-25-nor-24-acetoxymethyl-Avermectin (VIIn)

60 mg TES ether VIIm (52 μmol) was placed in 2 mL tetrahydrofuran at room temperature to which was added 100 μL HF·pyridine (25 g HF·pyridine, 10 mL pyridine, 25 mL tetrahydrofuran). After 10 minutes, 300 μL pyridine was added and the reaction was quenched at 0° C. with saturated sodium bicarbonate, extracted with ethyl acetate, washed with brine, and the organic layer dried with magnesium sulfate. The magnesium sulfate was filtered off and the solvent removed in vacuo. The crude was taken up in 2 mL methylene chloride at room temperature to which was added 100 μL Ac$_2$O and 250 μL pyridine and 1 mg N,N-dimethylaminopyridine. The reaction was stirred for 30 minutes at room temperature and the solution was purified directly by flash chromatography on silica gel with 2:1 hexanes:ethyl acetate to yield 50 mg (95%) of the title compound which was characterized by NMR.

EXAMPLE 54

Preparation of
4",5-Di-O-t-butyldimethylsilyl-7-O-trimethylsilyl-24-desmethyl-25-des(2-butyl)-22,23-dihydro-25-nor-24-n-octyl-Avermectin (VIIo)

85 mg aldehyde Va (81 μmol) was cooled to 0° C. in 3 mL tetrahydrofuran. To this was added 300 μL 1M n-octyl magnesium bromide (300 μmol) in ether. After 30 minutes, the reaction was quenched with saturated ammonium chloride and extracted with ethyl acetate. The organic layer was washed with brine, dried (magnesium sulfate), filtered and concentrated in vacuo. The crude was dissolved in 3 mL methylene chloride to which was added 2 mg pyridinium p-toluenesulfonate. After 1 hour at room temperature, 200 μL triethylamine was added, the solvent removed in vacuo and the crude purified on SiO$_2$ with 3:1 hexanes:ethyl acetate as eluant to yield 41 mg (45%) of the title compound which was characterized by NMR.

EXAMPLE 55

Preparation of
24-Desmethyl-25-des(2-butyl)-22,23-dihydro-25-nor-Avermectin (VIIIa)

45 mg VIIa was placed in 4 mL tetrahydrofuran at room temperature to which was added 1 mL HF·pyridine (25 g HF·pyridine, 10 mL pyridine, 25 mL tetrahydrofuran) and stirred for 48 hours. The reaction was poured into 25 mL water, and extracted once with ether. The aqueous layer was separated and neutralized with saturated sodium bicarbonate. The organic layer was washed with saturated sodium bicaronate, the aqueous layers combined and extracted with ether. The organic layers were pooled, washed with brine and dried over magnesium sulfate. The magnesium sulfate was filtered off and the solvent removed in vacuo. The crude was filtered through a short bed of silica gel using ethyl acetate as eluant and purified by reverse-phase preparative thin layer chromatography to yield 29 mg (85%) of the title compound which was characterized by NMR and mass spectra (797, M+7).

EXAMPLE 56

Preparation of
24-Desmethyl-25-des(2-butyl)-22,23-dihydro-25-nor-24-methyl-Avermectin (VIIIb)

Following the procedure outlined in Example 55, 112 mg trissilane VIIb was placed in 4 mL tetrahydrofuran with 1 mL HF·pyridine to afford 64 mg (75%) of the title compound which was characterized by NMR.

EXAMPLE 57

Preparation of
24-Desmethyl-25-des(2-butyl)-22,23-dihydro-25-nor-24-i-propyl-Avermectin (VIIIc)

Following the procedure outlined in Example 55, 150 mg trissilane VIIc was placed in 4 mL tetrahydrofuran with 1 mL HF·pyridine to afford 132 mg (88%) of the title compound which was characterized by NMR and mass spectra (839, M+7).

EXAMPLE 58

Preparation of
24-Desmethyl-25-des(2-butyl)-22,23-dihydro-25-nor-24-t-butyl-Avermectin (VIIId)

Following the procedure outlined in Example 55, 302 mg trissilane VIId was placed in 4 mL tetrahydrofuran with 1 mL HF·pyridine to afford 220 mg (100%) of the title compound which was characterized by NMR and mass spectra (853, M+7).

EXAMPLE 59

Preparation of
24-Desmethyl-25-des(2-butyl)-22,23-dihydro-25-nor-24-cyclohexyl-Avermectin (VIIIe)

Following the procedure outlined in Example 55, 207 mg trissilane (VIIe) was placed in 4 mL tetrahydrofuran with 1 mL HF·pyridine to afford 106 mg (66%) of the title compound which was characterized by NMR.

EXAMPLE 60

Preparation of
24-Desmethyl-25-des(2-butyl)-22,23-dihydro-25-nor-24-methoxy-Avermectin (VIIIf)

Following the procedure outlined in Example 55, 80 mg trissilane VIIf was placed in 4 mL tetrahydrofuran with 1 mL HF·pyridine to afford 41 mg (67%) of the title compound which was characterized by NMR and mass spectra (827, M+7).

EXAMPLE 61

Preparation of
24-Desmethyl-25-des(2-butyl)-22,23-dihydro-25-nor-24-phenyl-Avermectin (VIIIg)

Following the procedure outlined in Example 55, 181 mg trissilane VIIg was placed in 4 mL tetrahydrofuran with 1 mL HF·pyridine to afford 142 mg (78%) of the title compound which was characterized by NMR and mass spectra (873, M+7).

EXAMPLE 62

Preparation of
24-Desmethyl-25-des(2-butyl)-22,23-dihydro-25-nor-24-(4-fluoro)phenyl-Avermectin (VIIIh)

Following the procedure outlined in Example 55, 101 mg trissilane VIIh was placed in 4 mL tetrahydrofuran with 1 mL HF·pyridine to afford 59 mg (75%) of the title compound which was characterized by NMR and mass spectra (891, M+7).

EXAMPLE 63

Preparation of
24-Desmethyl-25-des(2-butyl)-22,23-dihydro-25-nor-24-(4-methoxy)phenyl-Avermectin (VIIIi)

Following the procedure outlined in Example 55, 102 mg trissilane VIIi was placed in 4 mL tetrahydrofuran with 1 mL HF·pyridine to afford 57 mg (71%) of the title compound which was characterized by NMR and mass spectra (903, M+7).

EXAMPLE 64

Preparation of
24-Desmethyl-25-des(2-butyl)-22,23-dihydro-25-nor-24-(2-furyl)-Avermectin (VIIIj)

Following the procedure outlined in Example 55, 50 mg trissilane VIIj was placed in 4 mL tetrahydrofuran with 1 mL HF·pyridine to afford 27 mg (73%) of the title compound which was characterized by NMR and mass spectra (863, M+7).

EXAMPLE 65

Preparation of
24-Desmethyl-25-des(2-butyl)-22,23-dihydro-25-nor-24-methoxymethyl-Avermectin (VIIIk)

Following the procedure outlined in Example 55, 150 mg trissilane VIIk was placed in 4 mL tetrahydrofuran with 1 mL HF·pyridine to afford 86 mg (78%) of the title compound which was characterized by NMR and mass spectra (841, M+7).

EXAMPLE 66

Preparation of
24-Desmethyl-25-des(2-butyl)-22,23-dihydro-25-nor-24-phenoxymethyl-Avermectin (VIIIl)

Following the procedure outlined in Example 55, 40 mg trissilane VIIl was placed in 4 mL tetrahydrofuran with 1 mL HF·pyridine to afford 25 mg (84%) of the title compound which was characterized by NMR and mass spectra (903, M+7).

EXAMPLE 67

Preparation of
24-Desmethyl-25-des(2-butyl)-22,23-dihydro-25-nor-24-acetoxymethyl-Avermectin Following the procedure outlined in Example 55, 60 mg trissilane VIII was placed in 4 mL tetrahydrofuran with 1 mL HF·pyridine to afford 41 mg (91%) of the title compound which was characterized by NMR.

EXAMPLE 68

Preparation of
24-Desmethyl-25-des(2-butyl)-22,23-dihydro-25-nor-24-n-octyl-Avermectin (VIIIp)

Following the procedure outlined in Example 55, 41 mg trissilane VIIp was placed in 4 mL tetrahydrofuran with 1 mL HF·pyridine to afford 27 mg (90%) of the title compound which was characterized by NMR and mass spectra (909, M+7).

EXAMPLE 69

Preparation of
24-Desmethyl-25-des(2-butyl)-22,23-dihydro-5-ketoxime-25-nor-24-phenyl-Avermectin 28 mg VIIIg was placed in 300 μL ethyl acetate at room temperature to which was added 100 mg manganese dioxide. After 20 minutes, the manganese dioxide was filtered off through a small plug of Celite using ethyl acetate as eluant and concentrated in vacuo. The 5-keto compound thus formed was dissolved in 1.5 mL ethyl acetate at room temperature to which was added 70 μL 1.0M zinc chloride in ether followed by 20 μL TMSONH$_2$ (181 μmol). After 2 hours at room temperature, 1 mL saturated sodium bicarbonate was added, the solution was stirred for 15 minutes, diluted with 2 mL water and extracted with ethyl acetate. The organic layer was dried over magnesium sulfate, filtered and concentrated in vacuo. The crude was purified by flash chromatography on silica gel using 4:96 methanol:methylene chloride as eluant to yield 24 mg (81%) of the title compound which was characterized by NMR and mass spectra (886, M+7).

EXAMPLE 70

Preparation of
24-Desmethyl-25-des(2-butyl)-22,23-dihydro-5-ketoxime-25-nor-24-t-butyl-Avermectin, isomer A Following the procedure in Example 69, 29 mg VIIId (isomer A) was converted into 23 mg (78%) of the title compound which was characterized by NMR and mass spectra (866, M+7).

EXAMPLE 71

Preparation of
24-Desmethyl-25-des(2-butyl)-22,23-dihydro-5-ketoxime-25-nor-24-t-butyl-Avermectin, isomer B Following the procedure in Example 69, 22 mg VIIId (isomer B) was converted into 22 mg (50%) of the title compound which was characterized by NMR and mass spectra (866, M+7).

EXAMPLE 72

Preparation of
24-Desmethyl-25-des(2-butyl)-22,23-dihydro-5-ketoxime-25-nor-24-i-propyl-Avermectin, isomer A Following the procedure in Example 69, 20 mg VIIIc (isomer A) was converted into 10 mg (49%) of the title compound which was characterized by NMR and mass spectra (852, M+7).

EXAMPLE 73

Preparation of
24-Desmethyl-25-des(2-butyl)-22,23-dihydro-5-ketoxime-25-nor-24-t-butyl-Avermectin, isomer B Following the procedure in Example 69, 20 mg of VIIIc (isomer B) was converted into 10 mg (49%) of the title compound which was characterized by NMR and mass spectra (852, M+7).

EXAMPLE 74

24-Desmethyl-25-des-(2-butyl)-22,23-dihydro-25-nor-24-tert-butyl Avermectin aglycone To a 50 mL flask containing 620 mg 24-des-methyl-25-des-(2-butyl)-22,23-dihydro-25-nor-24-tert-butyl avermectin (883 μmol) was added 20 mL methanol containing 200 μL concentrated sulfuric acid. The solution was stirred at room temperature for 20 hours and then poured into 40 mL 1:1 saturated NaHCO₃:saturated NaCl and extracted with methylene chloride. The organic layer was dried over MgSO₄, filtered and concentrated in vacuo. The crude residue was purified by flash chromatography on silica gel using 6:4 hexanes:ethyl acetate eluant. The yield of the aglycone was 458 mg (92%) of a clear glass. The C24 isomers could be further separated by reverse phase HPLC using 73:27 CH₃OH:-H₂O on a Waters C18 column.

EXAMPLE 75

5-O-tert
Butyldimethylsilyl-24-Desmethyl-25-des-(2-butyl)-22,23-dihydro-25-nor-24-tert-butyl Avermectin aglycone 458 Mg 24-desmethyl-25-des-(2-butyl)-22,23-dihydro-25-nor-24-tert-butyl avermectin aglycone (820 μmol) was placed in 5 mL THF to which was added 224 mg imidazole (3.28 mmol) and then 247 mg tert-butyl-dimethylsilyl chloride (1.64 mmol). The reaction was stirred for four hours at room temperature and then poured into 10 mL saturated NH₄Cl, extracted with ethyl acetate, washed with brine and dried over MgSO₄. The organic layer was filtered and the solvent removed in vacuo. The crude residue was purified by flash chromatography on silica gel using 3:1 hexanes:ethyl acetate as eluant to yield 479 mg (87%) of the desired product as a clear glass.

EXAMPLE 76

5-tert-Butyldimethylsilyl-24-desmethyl-25-des-(2-butyl)-22,23-dihydro-25-nor-24-tert-butyl Avermectin 660 Mg 24-desmethyl-25-des-(2-butyl)-22,23-dihydro-25-nor-24-tert-butyl avermectin (747 μmol) was placed in 5 mL THF to which was added 203 mg imidazole (2.98 mmol) and then 224 mg tert-butyl-dimethylsilyl chloride (1.49 mmol). The reaction was stirred for four hours at room temperature and then poured into 10 mL saturated NH₄Cl, extracted with ethyl acetate, washed with brine and dried over MgSO₄. The organic layer was filtered and the solvent removed in vacuo. The crude residue was purified by flash chromatography on silica gel using 3:1 hexanes:ethyl acetate as eluant to yield 479 mg (87%) of the desired product as a clear glass.

EXAMPLE 77

5-tert-Butyldimethylsilyl-24-desmethyl-25-des-(2-butyl)-22,23-dihydro-25-nor-4"-trifluoromethanesulfonyl-24-tert-butyl Avermectin 400 Mg 5-tert-butyldimethylsilyl-24-desmethyl-25-des-(2-butyl)-22,23-dihydro-25-nor-24-tert-butylavermectin (401 μmol) was placed in 5 mL methylene chloride at 0° C. To this was added 144 μL diisopropylethylamine (802 μmol) and 98 mg N,N-dimethylaminopyridine (802 nmol) followed by the dropwise addition of 135 μL trifluoromethanesulfonic anhydride (802 μmol). After one hour at 0° C., the solution was filtered through a 4 cm bed of silica gel using 1:1 hexanes:ethyl acetate as eluant and the solution was concentrated to yield 372 mg (81%) of the title compound as a light tan solid.

EXAMPLE 78

5-tert-Butyldimethylsilyl-24-desmethyl-25-des-(2-butyl)-22,23-dihydro-4"-deoxy-4"-β-(2-hydroxyethyl)thio-25-nor-24-tert-butyl Avermectin To a solution of 100 mg 5-tert-butyldimethylsilyl-24-desmethyl-25-des-2-(butyl)-22,23-dihydro-25-nor-4"-trifluormethansulfonyl-24-tert-butyl avermectin (87 μmol) in 2 mL dimethylformamide at room temperature is added 100 mL 2-mercaptoethanol, 100 mg K₂CO₃ and 5 mg 18-crown-6 (1,4,7,10,13,16-hexaoxacyclooctadecane). After stirring for several hours, this solution is poured into 20 mL brine and extracted with methylene chloride. The organic layer is dried over MgSO₄, filtered and concentrated in vacuo. The product is purified by flash chromatography on silica gel using 1:3 hexanes:ethyl acetate as eluant.

EXAMPLE 79

5-tert-Butyldimethylsilyl-24-desmethyl-25-des-(2-butyl)-22,23-dihydro-4"-deoxy-4"-β-methylthio-25-nor-24-tert-butyl Avermectin To a solution of 100 mg 5-tert-butyldimethylsilyl-24-desmethyl-25-des-2-(butyl)-22,23-dihydro-25-nor-4"-trifluormethansulfonyl-24-tert-butyl avermectin (87 μmol) in 2 mL dimethylformamide at 0° C. is added 6 mg MeSNA (87 μmol). After stirring for one hour, this solution is poured into 20 mL brine and extracted with methylene chloride. The organic layer is dried over MgSO₄, filtered and concentrated in vacuo. The product is purified by flash chromatography on silica gel using 3:1 hexanes:ethyl acetate as eluant.

EXAMPLE 80

24-Desmethyl-25-des-(2-butyl)-22,23-dihydro-25-nor-24-tert-butyl-5-O-tert-butyldimethylsilyl-13-O-methylethoxy-methoyl-avermectin aglycone 100 Mg of 24-desmethyl-25-des-(2-butyl)-22,23-dihydro-25-nor-24-tert-butyl-5-O-tert-butyldimethyl-silyl-avermectin aglycone (148 μmol) was placed in 2 mL of methyl chloride at room temperature to which was added 320 μL diisopropylethylamine (1.79 mmol), 43 mg N,N-dimethylaminopyridine (358 μmol) and 223 mg methoxyethoxymethyl chloride (1.79 mmol). The solution was stirred for 18 hours, poured into saturated NaHCO$_3$, extracted with methylene chloride, dried with MgSO$_4$, filtered and concentrated in vacuo. The crude material was purified by chromatography on silica gel with 85:15 hexanes:ethyl acetate as eluant to yield 78 mg product (69%) as a colorless glass.

EXAMPLE 81

24-Desmethyl-25-des-(2-butyl)-22,23-dihydro-25-nor-24-tert-butyl-13-O-methoxyethoxymethyl-avermectin aglycone 50 Mg of 24-desmethyl-25-des-(2-butyl)-22,23-dihydro-25-nor-24-tert-butyl-5-O-tert-butyldimethyl-silyl-13-O-methoxyethoxymethyl avermectin aglycone is placed in 4 mL THF at room temperature and 1 mL HF·pyridine (25 g HF·pyridine, 10 ml pyridine, 25 mL THF) is added and allowed to stir for twelve hours. The reaction is neutralized with saturated NaHCO$_3$, extracted with ethyl acetate, washed with brine and is dried organic layer over MgSO$_4$. The MgSO$_4$ is filtered, the filtrate is concentrated in vacuo and the crude material is purified by flash chromatography on silica gel with 1:1 hexanes:ethyl acetate as eluant. The product is characterized by its mass, 1H and 13C NMR spectra.

EXAMPLE 82

24-Desmethyl-25-des-(2-butyl)-22,23-dihydro-25-nor-24-tert-butyl-5-O-tert-butyldimethylsilyl-13-O-methoxymethyl-avermectin aglycone 100 Mg of 24-desmethyl-25-des-(2-butyl)-22,23-dihydro-25-nor-24-tert-butyl-5-O-tert-butyldimethyl-silyl-avermectin aglycone (148 μmol) is placed in 2 mL methylene chloride at room temperature and 320 μL diisopropylethylamine (1.79 mmol), 43 mg N,N-dimethyl-aminopyridine (358 μmol) and 144 mg methoxymethyl chloride (1.79 mmol) are added. The solution is stirred for 18 hours and poured into saturated NaHCO$_3$, extracted with methylene chloride and the organic layer is dried with MgSO$_4$. The MgSO$_4$ is filtered, the filtrate is concentrated in vacuo and the crude material is purified by chromatography on silica gel with 85:15 hexanes:ethyl acetate as eluant. The product is characterized by its mass, 1H and 13C NMR spectra.

EXAMPLE 83

24-Desmethyl-25-des-(2-butyl)-22,23-dihydro-25-nor-24-tert-butyl-13-O-methoxymethyl-avermectin aglycone 50 Mg of 24-desmethyl-25-des-(2-butyl)-22,23-dihydro-25-nor-24-tert-butyl-5-O-tert-butyldimethyl-silyl-13-O-methoxymethyl-avermectin aglycone is placed in 4 mL of THF at room temperature and 1 mL of HF·pyridine (25 g HF·pyridine, 10 ml pyridine, 25 mL THF) is added and allow to stir for twelve hours. The reaction is neutralized with saturated NaHCO$_3$, extracted with washed with brine and the organic layer is dried over MgSO$_4$. The MgSO$_4$ is filtered, the filtrate is concentrated in vacuo and the crude material is purified by flash chromatography on silica gel with 1:1 hexanes:ethyl acetate as eluant. The product is characterized by its mass, 1H and 13C NMR spectra.

EXAMPLE 84

24-Desmethyl-25-des-(2-butyl)-22,23-dihydro-25-nor-24-tert-butyl-5-O-tert-butyldimethylsilyl-13-deoxy-13-chloro-avermectin aglycone 100 Mg 24-desmethyl-25-des-(2-butyl)-22,23-dihydro-25-nor-24-tert-butyl-5-O-tert-butyldimethyl-silyl-avermectin aglycone (148 μmol) was placed in 2 mL methylene chloride to which was added 320 μL diisopropylethylamine (1.48 mmol), 43 mg N,N-dimethylaminopyridine (352 μmol) and 327 mg O-nitrobenzenesulfonyl chloride (1.48 mmol). This reaction was allowed to stir at room temperature for 6 hours and was then poured into saturated NaHCO$_3$, extracted with methylene chloride and dried over MgSO$_4$. The MgSO$_4$ was filtered off, the solution concentrated in vacuo and the crude material purified by flash chromatography on silica gel using 4:1 hexanes:ethyl acetate as eluant to yield 66 mg product (64%) as a colorless glass.

EXAMPLE 85

24-Desmethyl-25-des-(2-butyl)-22,23-dihydro-25-nor-24-tert-butyl-5-O-tert-butyldimethylsilyl-13-deoxy-avermectin aglycone 50 Mg of 24-desmethyl-25-des-(2-butyl)-22,23-dihydro-25-nor-24-tert-butyl-5-O-tert-butyldimethyl-silyl-13-chloro-13-deoxy-avermectin aglycone (72 μmol) is placed in 2 mL benzene and added to a solution of 42 mg of (nBu)$_3$SnH (144 μmol) in 5 mg of AIBN. This solution is heated to reflux for three hours, cooled to room temperature and purified directly by flash chromatography on silica gel to yield the desired product. The product is characterized by its mass, 1H and 13C NMR spectra.

EXAMPLE 86

24-Desmethyl-25-des-(2-butyl)-22,23-dihydro-25-nor-24-tert-butyl-13-deoxy-avermectin aglycone 50 Mg of 24-desmethyl-25-des-(2-butyl)-22,23-dihydro-25-nor-24-tert-butyl-5-O-tert-butyldimethyl-silyl-13-deoxy-avermectin aglycone is placed in 4 mL of THF at room temperature and 1 mL of HF·pyridine (25 g HF·pyridine, 10 ml pyridine, 25 mL THF) is added and allowed to stir for twelve hours. The reaction is neutralized with saturated NaHCO$_3$, extracted with ethyl acetate, washed with brine and the organic layer is dried over MgSO$_4$. The MgSO$_4$ is filtered, the filtrate is concentrated in vacuo and the crude is purified by flash chromatography on silica gel with 1:1 hexanes:ethyl acetate as eluant. The product is characterized by its mass, 1H and 13C NMR spectra.

EXAMPLE 87

24-Desmethyl-25-des-(2-butyl)-22,23-dihydro-25-nor-24-tert-butyl-5-O-tert-butyldimethylsilyl-7-O-trimethylsilyl-13-deoxy-13-fluoro-avermectin aglycone 100 Mg of 24-desmethyl-25-des-(2-butyl)-22,23-dihydro-25-nor-24-tert-butyl-5-O-tert-butyldimethyl-silyl-avermectin aglycone (148 μmol) is placed in 2 mL of methylene chloride at room temperature and 1 mL bis(trimethylsilyl)trifluroroacetamide is added and allowed to stir for 24 hours. The solvent and excess bis(trimethylsilyl)trifluoroacetamide are removed in vacuo and the product is placed in 2 mL of THF containing 1% glacial acetic acid. After 30 minutes, the reaction is quenched with saturated NaHCO$_3$, extracted with methylene chloride and organic layer is dried over MgSO$_4$. The MgSO$_4$ is filtered and the organic layer concentrated in vacuo. The crude material placed in 2 mL methylene chloride at 0° C. and to this solution is added 50 mg diethylaminosulfur trifluoride (310 μmol). After one hour at 0° C. the reaction is quenched with saturated NaHCO$_3$, extracted with methylene chloride and the organic layer is dried over MgSO$_4$. The MgSO$_4$ is filtered, the organic layer is concentrated in vacuo and the crude material is purified by flash chromatography on silica gel to yield the desired product. The product is characterized by its mass, 1H and 13C NMR spectra.

EXAMPLE 88

24-Desmethyl-25-des-(2-butyl)-22,23-dihydro-25-nor-24-tert-butyl-13-deoxy-13-fluoro-avermectin aglycone 50 Mg of 24-desmethyl-25-des-(2-butyl)-22,23-dihydro-25-nor-24-tert-butyl-5-O-tert-butyldimethyl-silyl-7-O-trimethylsilyl-13-deoxy-13-fluoro-avermectin aglycone is placed on 4 mL of THF at room temperature and 1 mL of HF·pyridine (25 g HF·pyridine, 10 ml pyridine, 25 mL THF) is added and allowed to stir for 48 hours. The reaction is neutralized with saturated NaHCO$_3$, extracted with ethyl acetate, washed with brine and the organic layer is dried over MgSO$_4$. The MgSO$_4$ is filtered, the filtrate is concentrated in vacuo and the crude material is purified by flash chromatography on silica gel with 1:1 hexanes:ethyl acetate as eluant. The product is characterized by its mass, 1H and 13C NMR spectra.

EXAMPLE 89

24-Desmethyl-25-des-(2-butyl)-22,23-dihydro-25-nor-24-tert-butyl-5-O-tert-butyldimethylsilyl-4''-oxo-avermectin 100 Mg of 24-desmethyl-25-des-(2-butyl)-22,23-dihydro-25-nor-24-tert-butyl-5-O-tert-butyldimethyl-silyl-avermectin (104 μmol) is placed in 2 mL of methylene chloride at 30° C. with 56 μL diisopropylethylamine (312 μmol) and 22 μL methyl sulfoxide (312 μmol). To this solution 44 μL phenylphosphonic dichloride (312 μmol) is added. This solution is allowed to slowly warm to room temperature over one hour. The reaction is quenched with saturated NaHCO$_3$, extracted with methylene chloride and the organic layer is dried over MgSO$_4$. The MgSO$_4$ is filtered, the organic layer is concentrated in vacuo and purified by flash chromatography on silica gel with 2:1 hexanes:ethyl acetate as eluant. The product is characterized by its mass, 1H and 13C NMR spectra.

EXAMPLE 90

24-Desmethyl-25-des-(2-butyl)-22,23-dihydro-25-nor-24-tert-butyl-5-O-tert-butyldimethylsilyl-4''-deoxy-4''epi-amino-avermectin 100 Mg of 24-desmethyl-25-des-(2-butyl)-22,23-dihydro-25-nor-24-tert-butyl-5-O-tert-butyldimethyl-silyl-4''-oxo-avermectin is placed 3 mL of methanol with 160 mg ammonium acetate and to this is added 12 mg of sodium cyanoborohydride. The reaction is stirred at room temperature for one hour and then poured into saturated NaHCO$_3$. The organic products are extracted with ethyl acetate and dried over MgSO$_4$. The MgSO$_4$ is filtered, the organic layer is concentrated in vacuo and the crude product purified by flash chromatography on silica gel using 98:2 methylene chloride:methanol as eluant to yield the desired product. The product is characterized by its mass, 1H and 13C NMR spectra.

EXAMPLE 91

24-Desmethyl-25-des-(2-butyl)-22,23-dihydro-25-nor-24-tert-butyl-5-O-tert-butyldimethylsilyl-4''-deoxy-4''-epi-acetylamino-avermectin 50 Mg of 24 desmethyl-25-des-(2-butyl)-22,23-dihydro-25-nor-24-tert-butyl-5-O-tert-butyldimethyl-silyl-4''-deoxy-4''epi-amino-avermectin is placed in 3 mL of methylene chloride at 0° C. and to this is added a solution of 200 μL of pyridine, 25 mg of N,N-dimethylaminopyridine and 100 μl of acetic anhydride. After three hours at 0° C., this material is purified directly by flash chromatography on silica gel. The product is characterized by its mass, 1H and 13C NMR spectra.

EXAMPLE 92

24-Desmethyl-25-des-(2-butyl)-22,23-dihydro-25-nor-24-tert-butyl-4''-deoxy-4''-epi-acetylamino-avermectin 50 Mg of 24-desmethyl-25-des-(2-butyl)-22,23-dihydro-25-nor-24-tert-butyl-5-O-tert-butyldimethyl-silyl-4''-deoxy-4''-epi-acetylamino-avermectin is placed in 4 mL of THF at room temperature and to it is added 1 mL of HF·pyridine (25 g HF·pyridine, 10 ml pyridine, 25 mL THF) and allowed to stir for 48 hours. The reaction is neutralized with saturated NaHCO$_3$, extracted with ethyl acetate, washed with brine and the organic layer is dried over MgSO$_4$. The MgSO$_4$ is filtered, the organic layer is concentrated in vacuo and the crude material purified by flash chromatography on silica gel. The product is characterized by its mass, 1H and 13C NMR spectra.

What is claimed is:

1. The compounds having the following structural formula:

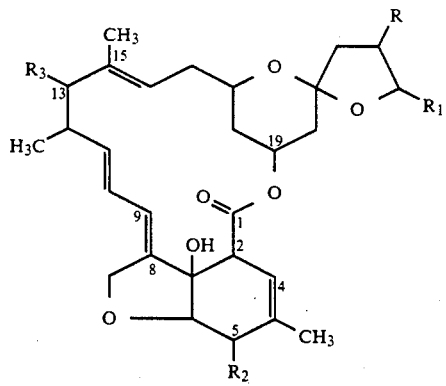

where R is hydrogen, $C_1$–$C_{10}$ alkyl, $C_2$–$C_{10}$ alkenyl or phenyl;

$R_1$ is hydrogen, $C_1$–$C_{10}$ alkyl, $C_2$–$C_{10}$ alkenyl, $C_1$–$C_{10}$ alkynyl, $C_1$–$C_{10}$ alkoxy-$C_1$–$C_{10}$ alkyl or $C_1$–$C_{10}$ alkylthio-$C_1$–$C_{10}$ alkyl group; a $C_3$–$C_8$ cycloalkyl or $C_5$–$C_8$ cycloalkenyl group, either of which may optionally be substituted by methylene or from 1 to 3 of $C_1-C_4$ alkyl groups or halo atoms; phenyl, phenoxy, $C_1-C_{10}$ alkyl phenyl, $C_2-C_{10}$ alkenyl phenyl, $C_2-C_{10}$ alkynyl phenyl, substituted $C_1-C_{10}$ alkyl wherein the substituents independently are 1 to 3 of $C_1-C_5$ alkyl, $C_3-C_8$ cycloalkyl or substituted $C_1-C_{10}$ alkyl wherein the substitutents are independently 1 to 3 of hydroxy, halogen, cyano, $C_1-C_5$ alkyl thio, $C_1-C_5$ alkyl sulfinyl, $C_1-C_5$ alkyl sulfonyl, amino, $C_1-C_5$ mono or dialkyl amino, $C_1-C_5$ alkanoyl amino or $C_1-C_5$ alkanoylthio;

$R_2$ is hydroxy, $C_1-C_{10}$ alkoxy, $C_1-C_{10}$ alkanoyloxy, oxo or oxime;

$R_3$ is hydrogen, hydroxy, $C_1-C_{10}$ alkyloxy, $C_1-C_8$ alkanoyloxy, $C_1-C_5$ alkoxy-$C_1-C_5$-alkoxy, $C_1-C_5$ alkoxy-$C_1-C_5$-alkoxy-$C_1-C_5$-alkoxy, halogen,

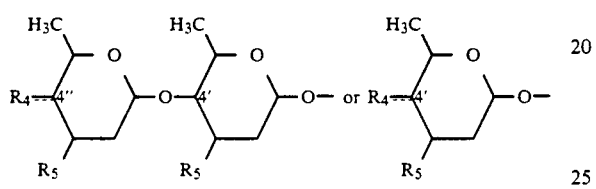

wherein $R_4$ is attached to C-4" or C-4' by a single bond and is hydroxy, amino, N-$C_1-C_8$ alkylamino, N,N-$C_1-C_8$-dialkylamino, N-$C_1-C_8$ alkanoylamino, N-$C_1-C_5$ alkyl $C_1-C_5$ alkanoylamino, tri $C_1-C_8$ alkylsilyloxy, $C_1-C_8$ alkylthio, $C_1-C_8$ alkyl sulfinyl, $C_1-C_8$ alkyl sulfonyl or substituted $C_1-C_8$ alkyl thio, sulfinyl or sulfonyl where the substituents are from 1 to 5 of hydroxy, halogen, amino or mono or di-$C_1-C_3$ alkylamino; or $R_4$ is attached to C-4" or C-4' by a double bond and is ketone, oxime, semicarbazono, N-$C_1-C_8$ alkylsemicarbazono, N,N-$C_1-C_8$ diloweralkylsemicarbazono, $C_1-C_8$ alkanoylhydrazono, benzoylhydrazono, or $C_1-C_8$ alkylbenzoyl-hydrazono; and each $R_5$ is independently hydroxy or $C_1-C_{10}$ alkoxy.

2. The compound of claim 1 wherein

R is hydrogen, $C_1-C_{10}$ alkyl, $C_2-C_{10}$ alkenyl or phenyl;

$R_1$ is hydrogen, $C_1-C_{10}$ alkyl, $C_1-C_{10}$ alkoxy, $C_1-C_5$ alkoxy-$C_1-C_5$ alkyl, $C_2-C_{10}$ alkenyl, or $C_3-C_8$ cycloalkyl, $C_5-C_6$ cycloalkenyl, phenyl, substituted $C_1-C_{10}$ alkyl, or substituted phenyl wherein the substituents are halogen, $C_1-C_5$ alkyl, or $C_3-C_8$ cycloalkyl, substituted $C_1-C_{10}$ alkyl wherein the substituents are 1 to 3 of hydroxy, halogen, cyano, $C_1-C_5$ alkylthio, alkylsulfinyl, alkylsulfonyl, or $C_1-C_5$ alkanoylamino;

$R_2$ is hydroxy, loweralkoxy or oxime;

$R_3$ is hydrogen, hydroxy, $C_1-C_{10}$ alkoxy, $C_1-C_8$ alkanoyloxy, $C_1-C_5$ alkoxy-$C_1-C_5$-alkoxy, $C_1-C_5$ alkoxy-$C_1-C_5$-alkoxy-$C_1-C_5$-alkoxy, halogen,

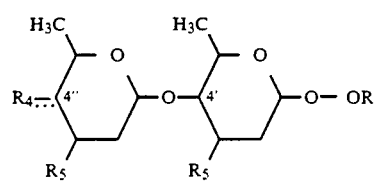

-continued

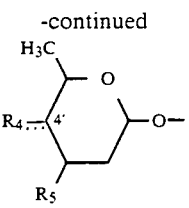

wherein $R_4$ is attached to C-4" or C-4' by a single bond and is hydroxy, amino, N-$C_1-C_8$ alkylamino, N,N-$C_1-C_8$-dialkylamino, N-$C_1-C_8$ alkanoylamino, or N-$C_1-C_5$ alkylalkanoylamino, $C_1-C_3$ alkyl thio, $C_1-C_3$ alkyl sulfinyl, $C_1-C_3$ alkyl sulfonyl or substituted $C_1-C_3$-alkyl thio, sulfinyl, or sulfonyl where the substituents are hydroxy, amino or trifluoro; or $R_4$ is attached to C-4" or C-4' by a double bond and is oxo; and each $R_5$ is independently hydroxy or $C_1-C_{10}$ alkoxy.

3. The compound of claim 2 wherein

R is hydrogen, $C_1-C_5$ alkyl, $C_2-C_5$ alkenyl or phenyl;

$R_1$ is hydrogen, $C_1-C_{10}$ alkyl, $C_1-C_{10}$ alkoxy $C_1-C_5$ alkoxy $C_1-C_5$ alkyl, $C_2-C_{10}$ alkenyl, or $C_3-C_8$ cycloalkyl, phenyl, substituted $C_1-C_{10}$ alkyl, or substituted phenyl wherein the substituents are fluoro, substituted $C_1-C_{10}$ alkyl wherein the substituents are 1 to 3 of halogen, cyano, $C_1-C_5$ alkylthio, alkylsulfonyl, or $C_1-C_5$ alkanoylamino;

$R_2$ is hydroxy, methoxy or oxime;

$R_3$ is hydrogen, hydroxy, $C_1-C_5$ alkoxy-$C_1-C_5$-alkoxy, $C_1-C_5$ alkoxy-$C_1-C_5$-alkoxy-$C_1-C_5$-alkoxy, halogen, or

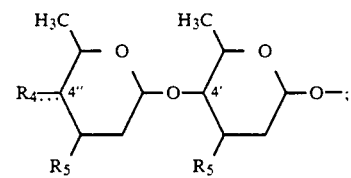

wherein $R_4$ is attached to C-4" or C-4' by a single bond and is hydroxy, amino, N-$C_1-C_3$ alkylamino, N,N-$C_1-C_3$-dialkylamino, N-$C_1-C_3$ alkanoylamino, or N-$C_1-C_3$ alkyl $C_1-C_5$ alkanoylamino; or $R_4$ is attached to C-4" or C-4' by a double bond and is oxo; and each $R_5$ is methoxy.

4. The compound of claim 3 wherein

R is hydrogen, $C_1-C_5$ alkyl, $C_2-C_5$ alkenyl or phenyl;

$R_1$ is hydrogen, $C_1-C_6$ alkyl, $C_1-C_4$ alkoxy, $C_1-C_3$ alkoxy $C_1-C_3$ alkyl, $C_2-C_6$ alkenyl, or $C_5-C_6$ cycloalkyl, phenyl, substituted $C_1-C_6$ alkyl, or substituted phenyl wherein the substituents are fluoro, substituted $C_1-C_6$ alkyl wherein the substituent is hydroxy, fluoro, chloro, $C_1-C_3$ alkylthio, or $C_1-C_3$ alkanoylamino;

$R_2$ is hydroxy, methoxy or oxime;

$R_3$ is hydrogen, hydroxy, $C_1-C_3$-alkoxy-$C_1-C_3$-alkoxy, $C_1-C_3$-alkoxy-$C_1-C_3$-alkoxy-$C_1-C_3$-alkoxy, halogen, or

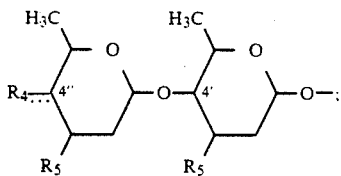

wherein R₄ is attached to C-4" or C-4' by a single bond and is hydroxy, amino, N—C₁-C₃ alkylamino, N,N—C₁-C₃-dialkylamino, N—C₁-C₃ alkanoylamino, or N—C₁-C₃ alkylalkanoylamino; and each R₅ is methoxy.

5. The compounds of claim 1 which are:
24-desmethyl-25-des-(2-butyl)-25-nor-24-cyanomethyl-22,23-dihydro avermectin Bla;
24-desmethyl-25-des-(2-butyl)-25-nor-24-methylthiomethyl-22,23-dihydro avermectin Bla;
24-desmethyl-25-des-(2-butyl)-25-nor-24-methylsulfoxymethyl-22,23-dihydro avermectin Bla;
24-desmethyl-25-des-(2-butyl)-25-nor-24-methylsulfonylmethyl-22,23-dihydro avermectin Bla;
24-desmethyl-25-des-(2-butyl)-25-nor-24-[4-(2-oxobut-3-ene)]-22,23-dihydro avermectin Bla;
24-desmethyl-25-des-(2-butyl)-25-nor-24-acetoxymethyl-22,23-dihydro avermectin Bla;
24-desmethyl-24-des-(2-butyl)-25-nor-24-fluoromethyl-22,23-dihydro avermectin Bla;
24-desmethyl-24-des-(2-butyl)-25-nor-24-[2-(4-methylpent-2-enyl)]-22,23-dihydro avermectin Bla; or
4"-deoxy-4"-epi-acetylamino-24-desmethyl-25-des-(2-butyl)-25-nor-24-isopropyl-22,23-dihydro avermectin Bla.

6. The compounds of claim 1 which are:
4"-deoxy-4"-epi-acetylamino-24-desmethyl-25-des-(2-butyl)-25-nor-24-tert-butyl-22,23-dihydro avermectin Bla;
4"-deoxy-4"-epi-amino-24-desmethyl-25-des-(2-butyl)-25-nor-24-tert-butyl-22,23-dihydro avermectin Bla;
4"-deoxy-4"-epi-acetylamino-24-desmethyl-25-des-(2-butyl)-25-nor-24-cyclohexyl-22,23-dihydro avermectin Bla;
4"-deoxy-4"-epi-acetylamino-24-desmethyl-25-des-(2-butyl)-25-nor-24-phenyl-22,23-dihydro avermectin Bla;
24-desmethyl-25-des-(2-butyl)-25-nor-24-phenyl avermectin-22,23-dihydro avermectin agylcone Bla;
24-desmethyl-25-des-(2-butyl)-25-nor-24-isopropyl-22,23-dihydro avermectin Bla agylcone;
24-desmethyl-25-des-(2-butyl)-25-nor-24-tert-butyl-22,23-dihydro avermectin Bla agylcone;
24-desmethyl-25-des-(2-butyl)-25-nor-24-cyclohexyl-22,23-dihydro avermectin Bla agylcone;
13-deoxy-13-fluoro-24-desmethyl-25-des-(2-butyl)-25-nor-24-phenyl-22,23-dihydro avermectin Bla agylcone;
13-deoxy-13-fluoro-24-desmethyl-25-des-(2-butyl)-25-nor-24-isopropyl-22,23-dihydro avermectin Bla agylcone;
13-deoxy-13-fluoro-24-desmethyl-24-des-(2-butyl)-25-nor-24-tert-butyl-22,23-dihydro avermectin Bla agylcone; or
24-des methyl-25-des-(2-butyl)-25-nor-24-(1-cyclohexenyl)-22,23-dihydro avermectin Bla.

7. The compounds of claim 1 which are:
13-O-methoxymethyl-24-desmethyl-25-des-(2-butyl)-25-nor-24-phenyl-22,23-dihydro avermectin Bla agylcone;
13-O-methoxymethyl-24-desmethyl-25-des-(2-butyl)-25-nor-24-isopropyl-22,23-dihydro avermectin Bla agylcone;
13-O-methoxymethyl-24-desmethyl-25-des-(2-butyl)-25-nor-24-cyclohexyl-22,23-dihydro avermectin Bla agylcone;
13-O-methoxymethyl-24-desmethyl-25-des-(2-butyl)-25-nor-24-tert-butyl-22,23-dihydro avermectin Bla agylcone;
13-O-methoxyethoxymethyl-24-desmethyl-25-des-(2-butyl)-25-nor-24-tert-butyl-22,23-dihydro avermectin Bla agylcone;
13-O-methoxyethoxymethyl-24-desmethyl-25-des-(2-butyl)-25-nor-24-isopropyl-22,23-dihydro avermectin Bla agylcone;
13-O-methoxyethoxymethyl-24-desmethyl-25-des-(2-butyl)-25-nor-24-cyclohexyl-22,23-dihydro avermectin Bla agylcone; or
13-O-methoxyethoxymethyl-24-desmethyl-25-des-(2-butyl)-25-nor-24-phenyl-22,23-dihydro avermectin Bla agylcone.

8. The compounds of claim 1 which are:
13-deoxy-24-desmethyl-25-des-(2-butyl)-25-nor-24-phenyl-22,23-dihydro avermectin Bla aglycone;
24-desmethyl-25-des(2-butyl)-22,23-dihydro-25-nor-avermectin Bla;
24-desmethyl-25-des(2-butyl)-22,23-dihydro-25-nor-24-methyl-avermectin Bla;
24-desmethyl-25-des(2-butyl)-22,23-dihydro-25-nor-24-i-propyl-avermectin Bla;
24-desmethyl-25-des(2-butyl)-22,23-dihydro-25-nor-24-t-butyl-avermectin Bla;
24-desmethyl-25-des(2-butyl)-22,23-dihydro-25-nor-24-cyclohexyl-avermectin Bla;
24-desmethyl-25-des(2-butyl)-22,23-dihydro-25-nor-24-methoxy-avermectin Bla;
24-desmethyl-25-des(2-butyl)-22,23-dihydro-25-nor-24-phenyl-avermectin Bla;
24-desmethyl-25-des(2-butyl)-22,23-dihydro-25-nor-24-(4-fluoro)phenyl-avermectin Bla; or
24-desmethyl-25-des(2-butyl)-22,23-dihydro-25-nor-24-(4-methoxy)phenyl-avermectin Bla.

9. The compounds of claim 1 which are:
24-desmethyl-25-des(2-butyl)-22,23-dihydro-25-nor-24-methoxymethyl-avermectin Bla;
24-desmethyl-25-des(2-butyl)-22,23-dihydro-25-nor-24-phenoxymethyl-avermectin Bla;
24-desmethyl-25-des(2-butyl)-22,23-dihydro-25-nor-24-n-octyl-avermectin Bla;
24-desmethyl-25-des(2-butyl)-22,23-dihydro-5-ketoxime-25-nor-24-phenyl-avermectin Bla;
24-desmethyl-25-des(2-butyl)-22,23-dihydro-5-ketoxime-25-nor-24-t-butyl-avermectin Bla isomer A;
24-desmethyl-25-des(2-butyl)-22,23-dihydro-5-ketoxime-25-nor-24-t-butyl-avermectin Bla isomer B;
24-desmethyl-25-des(2-butyl)-22,23-dihydro-5-ketoxime-25-nor-24-i-propyl-avermectin Bla isomer A;
24-desmethyl-25-des(2-butyl)-22,23-dihydro-5-ketoxime-25-nor-24-t-butyl-avermectin Bla isomer B;
13-deoxy-24-desmethyl-25-des-(2-butyl)-25-nor-22,23-dihydro-24-isopropyl-avermectin Bla aglycone;
13-deoxy-24-desmethyl-25-des-(2-butyl)-25-nor-22,23-dihydro-24-(t-butyl)-avermectin Bla aglycone;

13-deoxy-24-desmethyl-25-des-(2-butyl)-25-nor-22,23-dihydro-24-cyclohexyl-avermectin B1a aglycone;

13-deoxy-24-desmethyl-25-des-(2-butyl)-25-nor-22,23-dihydro-24-phenyl avermectin B1a aglycone.

10. A method for the treatment of parasitic infections in humans and animals which comprises administering to the human or animal in need of such treatment, an effective amount of a compound of claim 1.

11. A method for the treatment of parasitic infections of plants or plant products which comprises administering to such plants or plant products an effective amount of a compound of claim 1.

12. A method for the treatment of insect pest infestations which comprises applying an effective amount of a compound of claim 1 to the area infested with such insect pests.

13. A parasiticidal composition useful for treating parasitic infections of humans and animals and plants which comprises an inert carrier and a compound of claim 1.

14. A parasiticidal composition useful for applying to areas infested with insect pests which comprises an inert carrier and a compound of claim 1.

* * * * *